US006071520A

United States Patent [19]

Noteborn et al.

[11] Patent Number: 6,071,520

[45] Date of Patent: Jun. 6, 2000

[54] CHICKEN ANEMIA VIRUS MUTANTS AND VACCINES AND USES BASED ON THE VIRAL PROTEINS VP1, VP2 AND VP3 OR SEQUENCES OF THAT VIRUS CODING THEREFOR

[75] Inventors: Mathieu Hubertus Maria Noteborn, Leiden; Guus Koch, Lelystad, both of Netherlands

[73] Assignee: Leadd BV, Netherlands

[21] Appl. No.: 08/454,121

[22] PCT Filed: Jul. 19, 1994

[86] PCT No.: PCT/NL94/00168

§ 371 Date: Nov. 30, 1995

§ 102(e) Date: Nov. 30, 1995

[87] PCT Pub. No.: WO95/03414

PCT Pub. Date: Feb. 2, 1995

Related U.S. Application Data

[63] Continuation-in-part of application No. 08/030,335, filed as application No. PCT/NL91/00165, Sep. 11, 1991, Pat. No. 5,491,073.

[30] Foreign Application Priority Data

| | | | |
|---|---|---|---|
| Sep. 12, 1990 | [NL] | Netherlands | 9002008 |
| Sep. 11, 1991 | [WO] | WIPO | PCT/NL91/00165 |
| Jul. 20, 1993 | [NL] | Netherlands | 9301272 |

[51] Int. Cl.[7] ..... A61V 39/12

[52] U.S. Cl. ..... 424/186.1; 424/204.1

[58] Field of Search ..... 424/186.1; 435/204.1, 435/235.1, 5

[56] References Cited

U.S. PATENT DOCUMENTS 5,554,525 9/1996 Sondermeijer et al. .

FOREIGN PATENT DOCUMENTS 0483911 5/1992 European Pat. Off. .

0533294 3/1993 European Pat. Off. .

OTHER PUBLICATIONS

Meehan, B.M. et al. Arch. Virol., vol. 124, pp. 301–319, 1992.

Chandratilleke, D. et al. Avian Diseases, vol. 35, pp. 854–862, 1991.

Gelderbloom et al., (1989) *Archives of Virol.* 109:115–120.

Jeurissen et al., (1992) *J. Virol.* 66:7383–7388.

Noteborn et al., (1991) *J. Virol.* 65:3131–3139.

Noteborn et al., (1992) *Avian Pathology* 21:107–118.

Noteborn et al., (1992) *Gene* 118:267–271.

Noteborn et al., (1993) In: *Vaccines* 93, CSHL Press. Cold Spring Harbor, USA:299–304.

Ramakrishnan et al., (1993) *Nature* 362:217–223.

Todd et al., (1990) *J. General Virology* 71:819–823.

Todd et al., (1991) *Arch. Virol.* 117:129–135.

*Primary Examiner*—Mary E. Mosher
*Attorney, Agent, or Firm*—Rae-Venters Law Group, P.C.

[57] ABSTRACT

Novel proteins of the Chicken Anemia Virus are described and compositions for preventing or treating infections with that virus (CAV), in particular vaccines less pathogenic than the CAV itself, but yet leading to neutralizing antibodies in the immunized animal. Besides, there are described compositions containing antibodies against parts of the CAV for the control of infections with CAV and anti-idiotype antibodies. The invention also provides antibodies and test kits for the detection of CAV. Recombinant DNA molecules derived from CAV and host cells transfected therewith and vaccines based on these host cells are made possible by this invention. The invention also comprises living virus vaccines in which a piece of DNA is brought into a virus infectious to the host. Besides, the invention provides uses of proteins of CAV in the induction of apoptosis, in particular in tumor cells. It further provides the induction of cell death by means of gene therapy.

8 Claims, 12 Drawing Sheets

```
  M   A   R   R   A   R   R   P   R   G   R   F   Y   S   F   R   R   G   R   W
ATGGCAAGACGAGCTCGCAGACCGAGAGGCCGATTTTACTCCTTCAGAAGAGGACGGTGG                          912
  H   H   L   K   R   L   R   R   R   Y   K   F   R   H   R   R   R   Q   R   Y
CACCACCTCAAGCGACTTCGACGAAGATATAAATTTCGACATCGGAGGAGACAGCGGTAT                          972
  R   R   R   A   F   R   K   A   F   H   N   P   R   P   G   T   Y   S   V   R
CGTAGACGAGCTTTTAGGAAGGCCTTTCACAACCCCCGCCCCGGTACGTATAGTGTGAGG                         1032
  L   P   N   P   Q   S   T   M   T   I   R   F   Q   G   V   I   F   L   T   E
CTGCCGAACCCCCAATCTACTATGACTATCCGCTTCCAAGGGGTCATCTTTCTCACGGAA                         1092
  G   L   I   L   P   K   N   S   T   A   G   G   Y   A   D   H   M   Y   G   A
GGACTCATTCTGCCTAAAAACAGCACAGCGGGGGGCTATGCAGACCACATGTACGGGGCG                         1152
  R   V   A   K   I   S   V   N   L   K   E   F   L   L   A   S   M   N   L   T
AGAGTCGCCAAGATCTCTGTGAACCTGAAAGAGTTCCTGCTAGCCTCAATGAACCTGACA                         1212
  Y   V   S   K   I   G   G   P   I   A   G   E   L   I   A   D   G   S   K   S
TACGTGAGCAAAATCGGAGGCCCCATCGCCGGTGAGTTGATTGCGGACGGGTCTAAATCA                         1272
  Q   A   A   D   N   W   P   N   C   W   L   P   L   D   N   N   V   P   S   A
CAAGCCGCGGACAATTGGCCTAATTGCTGGCTGCCGCTAGATAATAACGTGCCCTCCGCT                         1332
  T   P   S   A   W   W   R   W   A   L   M   M   M   Q   P   T   D   S   C   R
ACACCATCGGCATGGTGGAGATGGGCCTTAATGATGATGCAGCCCACGGACTCTTGCCGG                         1392
  F   F   N   H   P   K   Q   M   T   L   Q   D   M   G   R   M   F   G   G   W
TTCTTTAATCACCCAAAGCAGATGACCCTGCAAGACATGGGTCGCATGTTTGGGGGCTGG                         1452
  H   L   F   R   H   I   E   T   R   F   Q   L   L   A   T   K   N   E   G   S
CACCTGTTCCGACACATTGAAACCCGCTTTCAGCTCCTTGCCACTAAGAATGAGGGATCC                         1512
  F   S   P   V   A   S   L   L   S   Q   G   E   Y   L   T   R   R   D   D   V
TTCAGCCCCGTGGCGAGTCTTCTCTCCCAGGGAGAGTACCTCACGCGTCGGGACGATGTT                         1572
  K   Y   S   S   D   H   Q   N   R   W   Q   K   G   G   Q   P   M   T   G   G
AAGTACAGCAGCGATCACCAGAACCGGTGGCAAAAGGCGGACAACCGATGACGGGGGC                           1632
  I   A   Y   A   T   G   K   M   R   P   D   E   Q   Q   Y   P   A   M   P   P
ATTGCTTATGCGACCGGGAAAATGAGACCCGACGAGCAACAGTACCCTGCTATGCCCCA                          1692
  D   P   P   I   I   T   A   T   T   A   Q   G   T   Q   V   R   C   M   N   S
GACCCCCCGATCATCACCGCTACTACAGCGCAAGGCACGCAAGTCCGCTGCATGAATAGC                         1752
  T   Q   A   W   W   S   W   D   T   Y   M   S   F   A   T   L   T   A   L   G
ACGCAAGCTTGGTGGTCATGGGACACATATATGAGCTTTGCAACACTCACAGCACTCGGT                         1812
  A   Q   W   S   F   P   P   G   Q   R   S   V   S   R   R   S   F   N   H   H
GCACAATGGTCTTTTCCTCCAGGGCAACGTTCAGTTTCTAGACGGTCCTTCAACCACCAC                         1872
  K   A   R   G   A   G   D   P   K   G   Q   R   W   H   T   L   V   P   L   G
AAGGCGAGAGGAGCCGGGGACCCCAAGGGCCAGAGATGGCACACGCTGGTGCCGCTCGGC                         1932
  T   E   T   I   T   D   S   Y   M   S   A   P   A   S   E   L   D   T   N   F
ACGGAGACCATCACCGACAGCTACATGTCAGCACCCGCATCAGAGCTGGACACTAATTTC                         1992
  F   T   L   Y   V   A   Q   G   T   N   K   S   Q   Q   Y   K   F   G   T   A
TTTACGCTTTACGTAGCGCAAGGCACAAATAAGTCGCAACAGTACAAGTTCGGCACAGCT                         2052
  T   Y   A   L   K   E   P   V   M   K   S   D   A   W   A   V   V   R   V   Q
ACATACGCGCTAAAGGAGCCGGTAATGAAGAGCGATGCATGGGCAGTGGTACGCGTCCAG                         2112
  S   V   W   Q   L   G   N   R   Q   R   P   Y   P   W   D   V   N   W   A   N
TCGGTCTGGCAGCTGGGTAACAGGCAGAGGCCATACCCATGGGACGTCAACTGGGCGAAC                         2172
  S   T   M   Y   W   G   T   Q   P   *
AGCACCATGTACTGGGGACGCAGCCCTGA                                                        2201
```

FIG. 1

```
      M   H   G   N   G   G   Q   P   A   A   G   G   S   E   S   A   L   S   R   E
ATGCACGGGAACGGCGGACAACCGGCCGCTGGGGGCAGTGAATCGGCGCTTAGCCGAGAG                          439
  G   Q   P   G   P   S   G   A   A   Q   G   Q   V   I   S   N   E   R   S   P
GGGCAACCTGGGCCCAGCGGAGCCGCGCAGGGGCAAGTAATTTCAAATGAACGCTCTCCA                          499
  R   R   Y   S   T   R   T   I   N   G   V   Q   A   T   N   K   F   T   A   V
AGAAGATACTCCACCCGGACCATCAACGGTGTTCAGGCCACCAACAAGTTCACGGCCGTT                          559
  G   N   P   S   L   Q   R   D   P   D   W   Y   R   W   N   Y   N   H   S   I
GGAAACCCCTCACTGCAGAGAGATCCGGATTGGTATCGCTGGAATTACAATCACTCTATC                          619
  A   V   W   L   R   E   C   S   R   S   H   A   K   I   C   N   G   Q   F
GCTGTGTGGCTGCGCGAATGCTCGCGCTCCCACGCTAAGATCTGCAACTGCGGACAATTC                          679
  R   K   H   W   F   Q   E   C   A   G   L   E   D   R   S   T   Q   A   S   L
AGAAAGCACTGGTTTCAAGAATGTGCCGGACTTGAGGACCGATCAACCCAAGCCTCCCTC                          739
  E   E   A   I   L   R   P   L   R   V   Q   G   K   R   A   K   R   K   L   D
GAAGAAGCGATCCTGCGACCCCTCCGAGTACAGGGTAAGCGAGCTAAAAGAAAGCTTGAT                          799
  Y   H   Y   S   Q   P   T   P   N   R   K   K   A   Y   K   T   V   R   W   Q
TACCACTACTCCCAGCCGACCCCGAACCGCAAAAAGGCGTATAAGACTGTAAGATGGCAA                          859
  D   E   L   A   D   R   E   A   D   F   T   P   S   E   E   D   G   T   T
GACGAGCTCGCAGACCGAGAGGCCGATTTTACTCCTTCAGAAGAGGACGGTGGCACCACC                          919
  S   S   D   F   D   E   D   I   N   F   D   I   G   G   D   S   G   I   V   D
TCAAGCGACTTCGACGAAGATATAAATTTCGACATCGGAGGAGACAGCGGTATCGTAGAC                          979
  E   L   L   G   R   P   F   T   T   P   A   P   V   R   I   V   *
GAGCTTTTAGGAAGGCCTTTCACAACCCCCGCCCCGGTACGTATAGTGTGA                                  1030
```

FIG. 2

```
  M   N   A   L   Q   E   D   T   P   P   G   P   S   T   V   F   R   P   P   T
ATGAACGCTCTCCAAGAAGATACTCCACCCGGACCATCAACGGTGTTCAGGCCACCAACA                        545
  S   S   R   P   L   E   T   P   H   C   R   E   I   R   I   G   I   A   G   I
AGTTCACGGCCGTTGGAAACCCCTCACTGCAGAGAGATCCGGATTGGTATCGCTGGAATT                        605
  T   I   T   L   S   L   C   G   C   A   N   A   R   A   P   T   L   R   S   A
ACAATCACTCTATCGCTGTGTGGCTGCGCGAATGCTCGCGCTCCCACGCTAAGATCTGCA                        665
  T   A   D   N   S   E   S   T   G   F   K   N   V   P   D   L   R   T   D   Q
ACTGCGGACAATTCAGAAAGCACTGGTTTCAAGAATGTGCCGGACTTGAGGACCGATCAA                        725
  P   K   P   P   S   K   K   R   S   C   D   P   S   E   Y   R   V   S   E   L
CCCAAGCCTCCCTCGAAGAAGCGATCCTGCGACCCCTCCGAGTACAGGGTAAGCGAGCTA                        785
  K   E   S   L   I   T   T   T   P   S   R   P   R   T   A   K   R   R   I   R
AAAGAAAGCTTGATTACCACTACTCCCAGCCGACCCCGAACCGCAAAAAGGCGTATAAGA                        845
  L   *
CTGTAA                                                                              851
```

FIG. 3

Amino-Acid Sequence of VP3.

```
1 -M  N  A  L  Q  E  D  T  P  P  G  P  S  T  V
   F  R  P  P  T  S  S  R  P  L  E  T  P  H  C
   R  E  I  R  I  G  I  A  G  I  T  I  T  L  S
   L  C  G  C  A  N  A  R  A  P  T  L  R  S  A
   T  A  D  N  S  E  S  T  G  F  K  N  V  P  D
   L  R  T  D  Q  P  K  P  P  S  K  K  R  S  C
   D  P  S  E  Y  R  V  S  E  L  K  E  S  L  I
   T  T  T  P  S  R  P  R  T  A  K  R  R  I  R
   L -121
```

CHICKEN ANEMIA VIRUS MUTANTS AND VACCINES AND USES BASED ON THE VIRAL PROTEINS VP1, VP2 AND VP3 OR SEQUENCES OF THAT VIRUS CODING THEREFOR

CROSS REFERENCE TO RELATED APPLICATIONS

This application is a National Stage filing of PCT/NL94/00168, filed Jul. 19, 1994. This application is a continuation-in-part of U.S. Ser. No. 08/030,335, filed Mar. 8, 1993, which has issued as U.S. Pat. No. 5,491,073, which is a National Stage filing of PCT/NL91/00165 filed Sep. 11, 1991.

The present invention relates to novel proteins and/or polypeptides of the Chicken Anemia Virus. Besides, it relates to vaccines and compositions for preventing or treating virus infections in poultry, in particular infections with the Chicken Anemia Virus (CAV).

In particular, the invention relates to vaccines that are less pathogenic than the CAV itself but yet lead to the generation of neutralizing antibodies in the immunized animal.

Besides, the invention relates to compositions containing antibodies against parts of the CAV for controlling infections with CAV. Also anti-idiotype antibodies which possess an immunogenicity corresponding with the antigen are a subject of the invention.

The invention also relates to antibodies for the detection or control of CAV infections. Also diagnostic test kits for the detection of CAV will be described.

The invention further relates to recombinant DNA molecules derived from CAV, which code for at least an immunogenic part of a CAV protein and host cells transfected with such recombinant DNA molecules. Vaccines based on these host cells are made possible by this invention.

Also so-called living virus vaccines, in which a piece of DNA coding for at least an immunogenic part of a CAV protein is brought into a virus infectious to the desired host, are a subject of the invention.

Processes for the prophylaxis or control of CAV infections, in particular in chickens, and processes for the preparation of recombinant parts of CAV comprising sequences, and processes for the preparation of vaccines are also subjects of the invention.

Besides, the invention relates to uses of the proteins of the CAV in the induction of apoptosis (programmed cell death). In particular, the proteins (polypeptides) can be used in the induction of apoptosis in tumor cells.

Besides, the proteins according to the invention can also be used in the elimination of other undesired cell populations, such as autoimmune reactive T cells in autoimmure diseases, such as rheumatoid arthritis, lupus, etc.

The invention further provides for the induction of cell death by means of gene therapy. Processes for preparing these therapeutics and processes for treatment therewith are also subjects of the invention.

The Chicken Anemia Virus (CAV) is a recently characterized DNA virus (Noteborn and De Boer. 1990). It belongs to a new virus family. In young chickens CAV causes anemia by destruction of erythroblastoid precursor cells and immune deficiency by depletion of thymocytes. Lesions occur in the spleen and liver (Jeurissen et al., 1989). A recent study has shown that the depletion of thymocytes is caused via apoptosis induced by CAV (Jeurissen et al., 1992b).

Gelderblom et al. (1989) and Todd et al. (1990) have shown by means of electron microscopic studies that CAV particles have a T3 icosahedron symmetry and a diameter of 23–25 nm. The CAV particles concentrate after equilibrium sedimentation at a density of 1.33–1.34 g/ml in CsCl.

Todd et al. (1990) have shown that isolated virus particles contain only one protein having a molecular weight of 50 kDa. The single-stranded DNA in the CAV particles is in the form of a circular minus strand (Gelderblom et al.; Todd et al., 1990; Noteborn et al., 1991). The replicative DNA intermediary was cloned and fully sequenced. The CAV genome is 2319 nucleotides long. On the basis of the genome structure and the DNA sequence the virus cannot be placed into one of the known virus families (Noteborn et al., 1991; Todd et al., 1991). The CAV genome contains three large, partially or completely overlapping reading frames coding for possible proteins having molecular weights of 51.6, 24.0 and 13.3 kDa. The CAV genome moreover contains one evident promoter/enhancer region and only one polyadenylation signal. Transcription of the replicative DNA intermediary produces a polyadenylated polycistronic RNA molecule of approximately 2100 nucleotides (Noteborn et al., 1992b).

Day-old chicks are most susceptible to CAV infections. In these animals lethargy, anorexia and anemia are observed from 10 days after inoculation with CAV. After infection mortality may increase to a maximum of 50%. With increasing age the resistance also increases. Jeurissen et al. (1992) have reposed that only the hematocrit values of chicks that had been infected with CAV at an age of 1–3 days are decreased. CAV infections of 1–21 days old chicks result in a depletion of in particular the thymus cortex. However, in older chickens CAV can subclinically multiply. CAV infection in older chickens can be determined by the occurrence of serum conversion (McIlroy et al., 1992).

The spread of CAV within a flock of chickens substantially occurs via contact infection. Most probable is ingestion of feces or other material contaminated with feces from CAV infected animals. Infection via the air, however, cannot be ruled out. Transmission of viruses to offspring via the egg is suggested by Yuasa et al. (1979) but by way of experiment vertical transmission of CAV from mother animals to chicks could not be demonstrated by us.

Immune deficiency resulting from the CAV induced depletion of the thymus cortex is considered to be the cause of disease symptoms occurring after secondary infections of normally non-pathogenic agents (De Boer et al., 1992; Engström, 1988; Rosenberger and Cloud, 1989; Von Bülow et al., 1986; Yuasa et al., 1980). Thus CAV is isolated in animals with Newcastle disease, Marek's disease, infectious bursitis (Gumboro) and in animals with 'blue wing disease' in association with reoviruses. CAV infections lead to increased inoculation reactions, e.g. against Newcastle disease virus.

Maternal antibodies have been found to give an important protection against CAV infection. A recent study under laboratory conditions has shown that maternal immune day-old chicks develop no CAV infection. Day-old chicks can also be protected passively by intravenous injection of antibodies from egg yolks of immune mother animals (De Boer et al., dates not published).

CAV can be multiplied in tissue culture. The titers then obtained are low in general. At present MDCC-MSB1 cells (Yuasa, 1983; Yuasa et al., 1983) are used therefor, in which CAV induces a cytopathogenic effect 48–72 hours after infection. MDCC-MSB1 cells are also used to determine neutralizing antibodies and antibodies directed against CAV by means of immunofluorescence (Von Bülow et al., 1985;

Chettle et al., 1991). It has not been found possible so far to attenuate the virulence of CAV by serial passage in MDCC-MSB1 cells.

Older animals do not develop disease syymptoms after CAV infection and chicks with maternal antibodies are protected. These data were used in Germany in a vaccination program based on controlled exposure to CAV of 14–16 weeks old mother animals. In the Netherlands this vaccination method is not allowed except at experimental level because of the attendant risks. As mentioned above, it is quite possible that CAM can be transmitted to offspring via the fertilized egg. McNulty et al. (1991) have recently shown that flocks that are CAV seropositive have production numbers inferior to those of CAV seronegative flocks. Moreover, Adair (personal communication) has shown immune deficiency in chickens having a subclinical CAV infection. The possible vertical virus spread and the immune deficiency caused by CAV with (sub)clinical infections renders a control program based on an innocuous vaccine very desirable.

In general, inactivated vaccines and subunit vaccines are the safest vaccines. The fact that under tissue culture conditions CAV multiplies only to low titers renders the preparation of an inactivated vaccine relatively expensive and laborious. For the preparation of a subunit vaccine against CAV infections those CAV proteins are necessary which induce a protective immune response in vaccinated chickens. Thus far only one protein (called VP1) has been found in purified CAV particles.

Surprisingly, it has now been found that this protein alone, as will further be shown in the Examples, is not capable of giving an immune response that protects against CAV infections. It has been found that in spite of the fact that VP1 seems to be the only protein present in the virus particle the VP2 protein now expressed by us for the first time is essential for generating virus neutralizing antibodies. Therefore, it is possible only now to develop an effective vaccine on the basis of parts of the virus.

We have cloned the three open reading frames present on the CAV genome into baculovirus vectors. The three CAV proteins VP1, VP2 and VP3 were expressed into Sf9 cells alone. in combination with one of the other CAV proteins or all three simultaneously by means of (co)-infection with recombinant CAV baculoviruses. Mother animals were injected with crude cell lysates which contained one or more CAV proteins. Only after immunization of chickens with antigen preparations containing proportional amounts of all three CAV proteins or containing essentially VP1 and VP2 and also some VP3, neutralizing antibodies developed. Eggs of such animals contained maternal antibodies against CAV. Infection tests with offspring of vaccinated mother animals showed that at least the CAV proteins VP1 and VP2 are necessary for the induction of a protective immune response. offspring of mother animals injected with all three CAV proteins were even better protected against infections with CAV. Injection into chickens with all three CAV proteins that had each individually been produced in Sf9 cells, induced few neutralizing antibodies against CAV. This implies that for an optimum induction of neutralizing antibodies against CAV, 2 or 3 CAV proteins must be synthesized together in an (insect) cell.

It is possible that fragments of 2 or 3 CAV proteins arc already sufficient to effect a protective immune response against CAV infections.

The recombinant CAV products, VP1+VP2 or VP1+VP2+VP3, which will be used for vaccination of laying-hens, can be synthesized by means of the baculovirus system. The CAV proteins can also be synthesized by means oft other systems, such as bacterial or yeast cells, via retro(viral) infection or gene amplification (CHO-dhfr system).

The fact that 2 or 3 proteins encoded by the open reading frames of the CAV genome can induce a protective immune response in chickens is also applicable to the development of living virus vectors. The coding sequences for VP1+VP2 or VP1+VP2+VP3 are then cloned into living virus vectors.

It is also possible that one of the CAV proteins VP1, VP2 or VP3, separately, but then within the context of a living virus vector, is also suitable for the induction of a protective immune response against CAV infections.

The expression of fragments of one or more above-mentioned CAV proteins by living virus vectors may be sufficient for the induction of a protective immune response.

In poultry, only living virus vectors which themselves show a good replication in the avian system can be used. Eligible for the use of viral vectors in chickens are, among other things: fowl pox virus, retroviral vectors, herpes virus vectors (Marek's virus and turkey herpes virus), adenoviruses and laryngotrachitis virus. It has been found that the induction of cell death as induced by CAV can essentially be attributed to VP3 and partly to VP2.

By deletion of the C terminal 11 amino acids of VP3 the induction of apoptosis by VP3 is strongly reduced. Consequently, the pathogenic activity of CAv can be drastically reduced by introduction of a stop codon into the C terminal region of VP3. The extra stop codon in the coding region for VP3 is introduced into the CAV clone pCAV/EcoRI (Noteborn and De Boer) which contains the complete CAV genome. The complete CAV mutant genome is cut from the vector and recycled. MDCC-MSB1 cells are transfected with the recycled CAV mutant DNA, and the virus of spring which are less pathogenic are harvested. Chickens are vaccinated with the attenuated CAV mutant viruses. Since the VP2 protein also has an effect on the induction of apcptosis, it is possible to also prepare attenuated CAV which contains a mutation in the coding region for VP2 or VP2 and VP3.

The above-mentioned introduction of a stop codon into the coding region for VP2 and/or VP3 can also be used in the production of CAV recombinant living virus vectors.

Animals infected with CAV at an older age develop no clinical symptoms. Yet it seems that such infections may lead to great economic losses for the poultry industry. Immunization of animals with the above-described recombinant CAV products will lead to an active protection against the above-mentioned subclinical symptoms.

The three CAV proteins which were expressed into the baculovirus system separately or in combination with one or two other CAV proteins can be used for tracing antibodies directed against CAV. Chickens infected or vaccinated with CAV can thus be traced. One or more CAV proteins can be used in immunoassays, such as 'enzyme-linked immunosorbent assay' (ELISA), immunoperoxidase staining and immunofluorescence assay. For measuring neutralizing antibodies two or more CAV proteins are required.

Immunization of mice with the 3 CAV recombinant products synthesized in insect cells with CAV recombinant baculoviruses finally produced monoclonal antibodies specific for VP2 and VP3. These monoclonals reacted with specific structures in CAV infected cells and not with uninfected cells.

By means of the antibodies generated with recombinant CAV proteins, CAV proteins can be traced in organ preparations of CAV-infected chickens. On the basis of these data, reliable diagnostic tests can be developed. The monoclonal and polyclonal antibodies according to the invention may also be used in other diagnostic assays, suchs as ELISAs, RIAs, SPIAs, immunofluorescence assays and immunoperoxidase staining, optionally together with one or more CAV proteins or fragments thereof.

In principle, all known embodiments of immunological diagnostic tests are possible with all available labels, and depending on the test to be carried out and the conditions under which it must be carried out, a person of ordinary skill in the art will be able to select the most suitable embodiment. Besides, for the purpose of this invention antibodies and/or other proteins/polypeptides are also derivatives and/or fragments, as far as they possess the desired activity. In the case of antibodies this means that they must at least be able to recognize the antigen.

The antibodies according to the invention may also be used for the passive immunization of poultry. Against the antibodies according to the invention, antibodies can be generated which are a so-called "internal image" of the antigen and can thus be used as such again, in particular in passive immunizations and diagnostics.

CAV induces apoptosis in infected thymocytes. It is possible that a CAV infection of (human) tumors also results in the cell death of the tumor cells.

In vitro the CAV protein VP3 is in itself capable of inducing apoptosis in chicken mononuclear tumor cells and in idiverse human tumor cells.

Expression of the CAV protein can therefore also be used for the induction of cell death in (human) tumors. The VP3 protein can be (transiently) expressed in rumors by means of DNA transfection. Expression of VP3 in (tumor) cells may also be take place by infecting the cells with (retro)viral vectors that contain a coding sequence for VP3. Administration to cells of non-viral components (e.g. liposomes or transferrin-derived vectors) containing VP3 proteins and/or coding sequences for VP3 is a further possibility for the expression/presence of VP3 in (tumor) cells.

The above-mentioned uses may also serve for the possible induction of cell death by expression in (tumor) cells of VP2 or VP2 together with VP3.

The CAV proteins VP2 and/or VP3 can be used in treatments for reducing (human) tumor formation. This may take place, e.g., by injecting the proteins according to the invention directly into a solid tumor or coupling the proteins to a ligand having affinity to a tutor associated antiligand. This coupling can be effected both chemically and (in case the ligand is also a protein) via making a recombinant fusion protein.

The chemical coupling can be effected directly or via a spacer group. Optionally, an inert carrier molecule may be selected, such as an indifferent serum protein, to which both the ligand and the viral protein are attached, whether or not via a spacer group.

Examples of frequently proposed combinations of ligand-antiligand interactions are ligand-receptor pairs, such as EGF/receptor, IL-2/receptor, /T cell receptor, antibody/tumor antigen, etc.

Preference is to be given to a ligand-antiligand combination that can be internalized by the cell. When a conjugate is selected, it can be advantageous to apply an intrinsic unstable group as a coupling between the viral protein and the ligand, so that the viral protein in the cell returns in native form. Not in all cases will it be necessary to select an internalizing combination. Tumor cells are metabolically active and will actively or passively take up substances, i.e. also the proteins according to the invention, via phagocytosis and/or pinocytosis.

The ligand to which the proteins according to the invention can be coupled in any manner whatsoever need not be a complete ligand. In general, it will be sufficient to use the antiligand binding part. Also derivatives of the ligands in question will be useful as long as they possess the antiligand binding activity. In case the ligand is an antibody, the fact is to be considered that antibodies of another origin than the type to which they are administered will in most cases lead to an immune response. Besides, this also applies to a number of other protein ligands.

It has meanwhile become sufficiently known that antibodies can be manipulated in such a manner that they generate no immune response but still recognize the desired antigen.

It will be briefly explained hereinafter how animal antibodies can be made suitable for human use (humanizing), but it may be clear that also adaptations of another type are possible.

In the first place, it is possible to chemically remove the constant part from the antibody to be humanized, so as to prepare FAB, FAB'2 or still smaller fragments (winter et al., 1990). In general, these fragments will at least be less immunogenic. Such fragments can also be prepared by means of recombinant DNA technology.

Besides, it is possible to replace the constant parts of animal antibodies by their human counterparts by means of recombinant DNA technology (Cabilly et al., 1984; Boss et al. 1984).

Besides, it is further possible to inoculate the antigen-binding domains of animal antibodies into antibodies of human origin (Winter et al., 1987).

Known tumor antigens against which antibodies have been generated are, e.g., CEA (carcino embryonic antigen) and the like.

The invention will be explained in more detail on the basis of the following experimental part. This is only for the purpose of illustration and should not be interpreted as a limitation of the scope of protection.

EXPERIMENAL

Baculovirus, Insect Cells and Chicken T Cells

The recombinant baculovirus pAcRP23-lacZ (Bishop, 1992) was obtained from Dr. R. Possee, NERC Institute of Virology, Oxford, England, and the genomic DNA was purified as described by Summers and Smith (1987). Spodoptera frugiperda (Sf9) cells were obtained from the American Tissue Cultuire Collection (no. CRL 1711). Baculovirus stocks were grown in confluent monolayers and suspension cultures in TC 100 medium (Gibco/BRL) containing 10% fetal calf serum as described by Summers and Smith (1987).

The T cell line MDCC-MSB1 transformed with Marek's disease virus (Yuasa, 1983; Yuasa et al., 1983) was grown in RPMI-1680 medium (Gibco/BRL) containing 10% fetal calf serum; the cells were used for DNA transfection experiments.

EXAMPLE 1

1.1 Cloning of CAV DNA

All CAV DNA sequences are originally derived from the plasmid DNA pIc-20H/CAV-EcoRI (Noteborn and De Boer, 1990). All cloning steps with plasmid DNA were in principle carried out according to the methods described by Maniatis et al. (1982).

The coding sequences of the three CAV proteins VP1, VP2 and VP3 were cloned separately into the baculovirus transfer vector pAcYM1 (Matsuura et al., 1987), which was obtained from Dr. D. H. L. Bishop, NERC Institute of Virology, Oxford, England. The coding sequence for the CAV protein VP3 and a mutant derived therefrom were cloned into the expression vector pRSV-H20 (Offringa et al.).

DNA transformations were carried out in the E. coli strain HB101. All plasmids were multiplied in large cultures under agitation, purified on CsCl gradients, and then by filtration over Sephacryl S-500 columns.

1.2 DNA Transfection

DNA of the recombinant baculovirus AcRP23-lacZ was isolated from extracellular baculoviruses according to a method described by Summers and Smith (1987). The lacZ gene contains a unique cutting site for the restriction enzyme Bsu361. The AcRP23-lacZ was linearized by digestion with Bsu361. Sf9 cells were transfected with calcium phosphate precipitates of linearized baculovirus AcRP23-lacZ DNA and recombinant transfer vector DNA according to the method oa Smith et al. (1983); this is an adaptation of the transfection. protocol of Graham and Van der Eb (1973) for Sf9 cells.

For the transfection of the diverse human and chicken cell lines 10 micrograms of pRSV-VP3, pCMV-VP3, pRSV-tr or pRSV-tr DNA were resuspended in 25 microliters of Milli-Q water and mixed with 260 microliters of TBS buffer. 15 Microliters of 10 mg/ml DEAE dextran were added to the DNA mixture which was incubated for 30 minutes at room temperature.

The cells were centrifuged at 1500 rpm in a table centrifuge. The medium was replaced by 5 ml TBS buffer, and the cells were carefully resuspended. The cells were pelleted and the TBS buffer was removed. The cell pellet was carefully resuspended in 300 microliters of DEAE dextran/DNA mix and incubated for 30 minutes at room temperature. 0.5 ml 25% DMSO/TBS were added, and the suspension was incubated for 3 minutes at room temperature. 5 ml TBS were added, and the cells were centrifuged at 1500 rpm in a table centrifuge. The supernatant was removed, and 5 ml. tissue medium were added. The cells were resuspended, centrifuged, taken up in 5 ml tissue culture medium and incubated at 37° C.—5% $CO_2$.

1.3 Selection of Recominant CAV Baculovirus

The supernatants containing extracellular baculoviruses were analyzed in a plaque assay with neutral red (Brown and Faulkner, 1977) and X-gal (Brown et al., 1991). The lacZ-negative plaques were inoculated on a monolayer of Sf9 ceils in microtiter dishes. Five days after infection the supernatants were harvested and stored at 4° C. The cell lysates were analyzed in a dot slot hybridization assay with p-labeled pIc-20H/CAV-EcoRI DNA as a probe.

Monolayers of Sf9 cells were inoculated with supernatants of cell lysates which strongly hybridized with the labeled CAV DNA probe. Two days after infection the cells were labeled with 3H-leucine. The proteins were separated on 14% polyacrylamide (PAA) SDS gels (Laemmli, 1970), made visible by means of a fluorography method and tested for the presence of specific recombinant CAV protein and the absence of the β-galactosidase protein.

1.4 Synthesis of Crude CAV Protein Preparations

Recombinant CAV baculoviruses which expressed the expected CAV protein in infected Sf9 cells, were dished up according to the method described by Summers and Smith (1983). Monolayers of Sf9 cells were infected with one type of recombinant CAV, baculovirus having a multiplicity of infection (moi) of approximately 5 plaque-forming units (pfu) per cell. Co-infections of 2 or 3 different CAV recombinant baculoviruses were carried out on Sf9 cell monolayers having a moi of 10 pfu of each recombinant CAV baculovirus per cell. Three days after infection the infected Sf9 cells were harvested. The crude cell lysates were suspended in PBS buffer.

EXAMPLE II 2.1 Immunization of Chickens with CAV-Specific Proteins

Groups of 6 weeks old chicken were injected intraperitoneally and subcutaneously with crude lysates emulsified in complete Freund's adjuvant of $10^6$ or $10^8$ Sf9 cells which were infected with one or more recombinant CAV baculoviruses. As a control a group of 8 animals were injected per immunization experiment with PBS buffer emulsified in complete Freund's adjuvant. On different days after immunization blood was collected, and the serum was analyzed for neutralizing antibodies directed against CAV.

2.2 Immunization of Mother Animals Against CAV

Four groups of each 16 hens were injected with crude lysates of $2 \times 10^7$ Sf9 cells, which were simultaneously infected with VP1, VP2, and VP3 recombinant baculoviruses; or with VP1 and VP2; or with VP1 and VP3; or with VP2 and VP3 recombinant baculoviruses. The cell lysates were emulsified in an equal volume of complete Freund's adjuvant. As a control a group of 16 hens was injected with PBS buffer in complete Freund's adjuvant. Yolk material of eggs of hens injected with these lysates or with PBS buffer was extracted with chloroform and analyzed for the presence of neutralizing antibodies,

EXAMPLE III 3.1 Production and Characterization of Mononclonal Antibodies Specifically Directed Against CAV Proteins The monoclonal antibody CVI-CAV-85.1 was obtained by injecting mice intraperitoneally with CAV injected MDCC-MSB1 cells with incomplete Freund's adjuvant. Finally, spleen cells of the immunized mice were fused with P3X63-Ag8.653 myeloma cells (Noteborn et al., 1991).

The other monoclonal antibodies directed against CAV antigens were obtained by injecting crude extracts of Sf9 cells infected with the three CAV recombinant baculoviruses into the spleen of 4 BALB/c mice. The sera of the immunized mice were tested for 7 weeks after immunization for neutralizing antibodies against CAV. The spleen cells of the immunized mice were fused with P3X63-Ag8.653 myeloma cells. Antibodies directed against CAV antigens were tested by different ways: a serum neutralization test; ELISAs based on purified CAV and on crude lysates of Sf9 cells infected with CAV recombinant baculovirus; immunofluorescence tests on CAV infected MDCC-MSB1 or on Sf9 cells infected with CAV recombinant baculovirus; Western blots of crude lysates of Sf9 cells infected with CAV recombinant baculovirus, and immunoperoxidase staining on thymus coupes of CAV infected chickens.

EXAMPLE IV 4.1 In Vitro Neutralization Test

The sera of chickens and mice injected with crude Sf9 cell lysates or PBS buffer were diluted 1:2 or 1:4 and then a two-fold dilution series was made. The diluted sera were incubated for 1 hour with $10^4$–$10^5$ $TCID_{50}$ CAV-Cux-1 (Von Bülow et al., 1983; Von Bülow, 1985). Approximately one hundred thousand cells of the T cell line MDCC-MSB1 transformed by Marek's disease virus were infected with this mixture of diluted sera and virus. As controls MDCC-MSB1 cells were infected with CAV which was neutralized with a positive CAV antiserum and a negative serum originating from specitic pathogen free chickens.

4.2 CAV Challenge Experiments

Fertilized eggs of the five groups of immunized hens were hatched. The chicks were injected intramuscularly on day 1 with $10^{5.5}$ TCID$_{50}$ CAV-Cux-1. On 6 and on 14 days after infection 5 chickens per group were subjected to section. The thymus was analyzed macroscopically and immunohistologically. Also, heparin blood was taken, and the blood cells were tested in a virus reisolation assay. Fourteen days after infection heparin blood was collected from all animals to determine the hematocrit.

EXAMPLE V

5.1 Immunohistologv and Immunofluorescence

Frozen coupes of thymus and bone marrow were made and used for immunoperoxidase staining with CAV-specific monoclonal antibodies, as described by Jeurissen et al. (1988).

Cells were fixed with 80% acetone and used for imunofluorescence tests with CAV-specific monoclonal antibodies and goat anti-mouse IgC conjugated with fluorescein isothiocyanate (Noteborn et al, 1990).

5.2 Detention of CAV in Blood Samples

Blood samples of CAV infected chicks were washed thrice with PBS and taken up in 1 ml. Twenty microliters of the cell suspension obtained were added to $10^5$ MDCC-MSB1 cells. The MDCC-MSB1 cells were 10 times diluted every 4–5 days, transferred to fresh culture medium, until a CAV-specific cytopathogenic effect became visible. If after 10 passages no cytopathogenic effect could be observed yet, then the virus isolation was considered to be negative. The number of times of passage is a measure for the amount of infectious CAV present in the blood of the infected chicks.

Results and Discussion

Construction of Recombinant CAV Transter Vectors

The CAV genome contains three large open reading frames which partially or completely overlap each other. By using start codons in different reading frames the CAV genome codes for 3 unique proteins. The coding sequences for the CAV proteins were separately (VP1, FIG. 1; VP2, FIG. 2; and VP3, FIG. 3) cloned into the baculovirus transfer vector pAcYM1. Because the VP3 reading frame completely falls within the VP2 reading frame, VP3, in case of expression of VP2, is always synthesized too, though in a clearly lesser degree. The transfer vector pAcYM1 lacks the coding sequences for polyhedrin, the polyhedrin promoter inclusively contains the A-residue of the start codon for the polyhedrin gene and the 3'-non-coding sequences including the polyadenylation signal. On both sides of the polyhedrin sequences are flanking viral sequences. The transfer vector contains prokaryote sequences for multiplication in bacteria (Matsuura et al., 1987).

The plasmid pEP-51.6 (Noteborn et al., 1992a) contains CAV DNA sequences of positions 791 to 2319. The CAV DNA insertion contains the complete coding region for the protein VP1 flanked by 62 bp 5'- an 117 bp 3'-non-coding DNA sequences. The plasmid pEP-51.6 was partially cut with HindIII, then completely cut with ECORI, and the 'sticky ends' were filled by means of Klenow polymerase. A 1.53 kb CAV DNA fragment was isolated. The plasmid pAcYM1 was linearized with BamHI, the sticky ends filled by means of Klenow polymerase and finally treated with alkaline phosphatase (CIP). The 1.53 kb CAV DNA fragment was ligated at the linearized pAcYM1 DNA. The orientation of VP1 in pAcYM1 DNA was determined by restriction enzyme analysis, and the final construct pAcVP1 is shown in FIG. 4.

Plasmid pEP-24.0 (Noteborn et al., dates not published) contains the 1.15 kb BamHI DNA fragment with CAV DNA sequences of positions 354 to 1508 (Noteborn and De Boer, 1990). This CAV DNA fragment contains the coding region for VP2 flanked by 26 bp 5'- and 484 bp 3'-non-coding DNA sequences. 106 bp downstream of the start codon for VP2 the start codon for VP3 is found in another reading frame, and the other coding sequence for VP3. The plasmid pEP-24.0 was treated with BamHI; the 1.15 kb DNA fragment was isolated and ligated at the BamHI linearized and CIP treated 9.3 kb pAcYM1 plasmid. The final DNA construct pAcVP2 was characterized with restriction enzymes and is shown in FIG. 4.

Plasmid pEP-13.3 (Noteborn et al., dates not published) contains the 0.46 kb BamHI-EcoRI DNA fragment with CAV DNA sequences of positions 427 to 868 (Noteborn and De Boer, 1990). The CAV DNA fragment contains the coding region for VP3, 58 bp 5'- and 25 bp 3'-non-coding DNA sequences. Plasmid pEP-13.3 was cut with the restriction enzymes BamHI and EcoRI, and a 0.46 kb BamHI-EcoRI fragment was isolated. Transfer vector pAcYM1 DNA was linearized with BamHI and treated with CIP, and a 9.3 kb fragment was isolated, The two synthetic DNA oligomers 5'-GATCCAACCCGGGTTG-3' (SEQ ID NO:1) and 5'-AATTCAACCCGGGTTG-3' (SEQ ID NO:2) were hybridized to each other and together form a BamHI-EcoRI DNA linker. The DNA linker was ligated at the 0.46 BamHI-EcoRI, and the 9.3 kb BamHI DNA fragment. The final construct pAc-VP3 was analyzed by restriction enzyme digestions and is shown in FIG. 4.

Construction of Recombinant CAV Baculovirus

Each of the three recombinant CAV transfer vectors was transfected separately, together with the recombinant baculovirus AcRP23-lacZ DNA, in Sf9 cells. Transfection occurred with "naked" baculovirus DNA and transfer vector DNA. This baculovirus genome contains, instead of the polyhedrin gene, the lac gen, under the regulation of the polyhedrin promoter. After homologous recombination baculoviruses were obtained which had always incorporated one of the three CAV genes instead of the lacZ gene and thus under regulation of the promoter of the polyhedrin gene. The baculoviruses which have correctly incorporated the CAV gene no longer contain the lacZ gene. In the first instance, the recombinant CAV viruses were characterized for the absence of β-galactosidase activity in plaques of baculovirus infected insect cells. Further the integration of CAV DNA sequences in the baculovirus genome was determined by means of a CAV-specific DNA probe in a hybridization experiment.

Exression of the CAV Proteins in Sf9 Cells

The expression of the specific CAV proteins in Sf9 cells infected with recombinant CAV was analyzed by protein labeling with 3H-leucine and PAA-SDS gel electrophoresis.

The CAV protein VP1 has a calculated molecular weight of 51.6 kDa (Noteborn and De Boer, 1990). Lysates of insect cells infected with recombinant VP1 baculovirus contain a protein of 52 kDa beside baculoviral and cellular products. The 52 kDa protein was absent in lysates of insect cells infected with the baculovirus AcRP23-lacZ and in non-infected cells. In vitro expression of the coding sequence of VP1 resulted in a protein of 52 kDa (Noteborn and De Boer, 1992). Most probably, VP1 is not glycosylated because VP1 which is synthesized in a rabbit reticulocyte lysate and VP1 synthesized in insect cells have the same molecular weight.

Translation of the gene coding for VP2, but also containing all coding sequences for VP3, produced in an in vitro system specific CAV proteins of 30 and 28 kDa and a minor amount of a 16 kDa protein product. Translation of only the open reading frame coding for VP3 in an in vitro system, however, produced only a protein of 16 kDa. Expression of VP2 by recombinant VP2 baculovirus in infected insect cells produced specific products of approximately 28 kDa and 30 kDa. Sf9 cells infected with a recombinant-lacZ baculovirus do not contain these CAV-specific proteins. The CAV-specific product of 16 kDa could mostly be demonstrated in very small amounts only. These data show that the recombinant VP2 baculovirus strongly expresses the protein VP2 and expresses VP3 in but a minor degree. A possible explanation thereof is that an internal start codon in a gene lying on the baculovirus genome is used very inefficiently.

Recombinant VP3 baculovirus synthesized in infected insect cells a main product of 16 kDa and small amounts of some proteins having molecular weights of approximately 21,000 and 12,000–14,000. In an immunofluorescence assay the CAV-specific monoclonal antibody CVI-CAV-85.1 reacted specifically with Sf9 cells expressing VP3. This monoclonal antibody precipitated specifically only a protein having a molecular weight of 16,000 from lysates of radioactively labeled Sf9 cells infected with VP3 recombinant baculovirus. In a pepscan analysis (Geysen et al., 1984) the epitope of the monoclonal antibody CVI-CAV-85.1 was localized on the N-terminus cf VP3. The pepscan analysis is shown in FIG. 5.

Induction of Neutralizing Antibodies in Chickens Immunized with Recombinant CAV Proteins In case of chicken anemia it has been determined that neutralizing antibodies properly correlate with protection. The CAV protein or several CAV proteins inducing neutralizing antibodies in chickens thus form the basis of a subunit vaccine.

In the first instance we have examined which CAV protein is capable of inducing antibodies against CAV neutralizing in chickens. Groups of 8 chickens at an age of approximately 6 weeks were injected with lysates of $10^6$ or $10^8$ recombinant CAV-infected Sf9 cells emulsified in complete Freund's adjuvant. As a control a group of 8 chickens was injected with PBS buffer emulsified in complete Freund's adjuvant. Before the immunization and 2, 4 and 6 weeks after immunization blood samples were taken. None of the control animals injected with PBS in complete Freund's adjuvant developed neutralizing antibodies against CAV (Table 1). Also chickens injected with lysates of $10^6$ or $10^8$ insect cells infected with recombinant VP2 or recombinant VP3 baculoviruses developed no neutralizing antibodies against CAV. Of the chickens injected with lysate of $10^6$ infected recombinant VP1 baculovirus insect cells three chickens, and of the chickens injected with a dosis of $10^8$ infected cells two chickens developed low titers varying between 1:8 and 1:32.

We conclude that the three recombinant CAV proteins, if injected separately into the chicken, induce no or only very slightly neutralizing antibodies against CAV.

Subsequently, we have studied whether the combination of the three recombinant CAV proteins is capable of inducing neutralizing antibodies in the chicken. To this end, Sf9 cells were infected simultaneously with the three recombinant CAV baculoviruses. Crude lysates of $10^6$ or $10^8$ of the infected cells, which therefore contained recombinant VP1+VP2+VP3, were prepared. Groups of eight chickens at an age of 6–8 weeks were injected with these lysates emulsified in complete Freund's adjuvant. As a control a group of eight chickens was injected with PBS buffer emulsified in complete Freund's adjuvant. Five weeks after immunization the eight chickens immunized with lysate of $10^6$ infected cells were all found to have neutralizing titers between 32 and 256, whereas seven of the eight animals immunized with $10^8$ cells had titers between 16 and 512 (Table 2a). Seven weeks after immunization all the animals of both groups were found to have developed a neutralizing titer against CAV. The group of chickens injected with PBS buffer was found to have developed no demonstrable neutralizing immune response against CAV.

Is it really necessary for the induction of neutralizing antibodies against CAV that the three CAV proteins are synthesized simultaneously in insect calls? To answer this question, Sf9 cells were infected separately with VP1, VP2 and VP3 recombinant baculoviruses. Then the crude cell lysates were combined, mixed with Freund's adjuvant and injected into a group of 8 chickens. As control preparations a crude lysate of Sf9 cells which all synthesized the 3 CAV proteins simultaneously and PBS buffer were used. Both preparations were emulsified in complete Freund's adjuvant and then injected into separate groups of each 8 chickens.

Sera of the group of chickens injected with crude lysates of Sf9 cells in which the 3 CAV proteins were synthesized separately were found to contain no or only very few neutralizing antibodies against CAV. However, the animals of the control group injected with crude lysates of Sf9 cells which together synthesized the 3 CAV proteins were found, as expected, to have developed a neutralizing immune response.

The animals injected with PBS buffer were found to be negative (Table 2b).

Neutralizing Antibodies in Eggs of Immunized Mother Animals

The above immunization experiments shoved that 3 recombinant CAV proteins expressed together in Sf9 cells induced neutralizing antibodies against CAV. In a next experiment it was examined whether combinations of 2 CAV proteins were also capable of inducing neutralizing antibodies. Here the antibodies in the yolks of eggs of immunized mother animals were measured.

Four groups of 16 chickens at an age of 33 weeks were injected with crude lysate of Sf9 cells which had been infected simultaneously with different combinations of recombinant CAV baculoviruses. The preparations containing either VP1+VP2+VP3 or VP1+VP2 induced in most animals neutralizing antibodies clearly demonstrable in their eggs (Table 3). The eggs of chickens injected with preparations containing either VP1+VP3 or VP2+VP3 were found to have no clear neutralizing antibody titer in the yolks. Only the yolks of eggs of one of the examined chickens were found to contain low titers of neutralizing antibodies. The eggs of the control group of 16 chickens injected with PBS buffer were tound to contain no neutralizing antibodies.

The data from the above-mentioned experiments with recombinant CAV proteins show that VP1+VP2 together are necessary and sufficient for the induction of neutralizing antibodies against CAV infections. However, a minor amount of VP3 in the VP1+VP2 preparations cannot be ruled out.

Protection Against CAV Challenge in Offspring of Immunized Chickens

Maternal antibodies protect young chicks against clinical symptoms caused by a CAV infection. We have studied which group(s) of chickens immunized with specific recombinant CAV proteins produced offspring protected against CAV challenge. Here virus was isolated and clinical symptoms characteristic of CAV were observed: atrophy of the thymus, decreased hemdtocrit and increased mortality.

Groups of between 23 and 35 day-old offspring were challenged with a high dosis of CAV. Six days after infection 5 animals subjected to section and having mother animals injected with PBS buffer, were all found to have a macroscopically visibly reduced thymus. In case of offspring of mother animals injected with recombinant VP2+VP3, 4 of the 5 animals had a small thymus. However, the 5 offspring, subjected to section, of mother animals injected with the 3 recombinant CAV proteins together were all found to have a normal thymus. In the group of offspring of mother animals treated with VP1+VP2 only 1 of the 5 animals examined was found to have a reduced thymus (Table 4). Fourteen days after infection, again 5 animals per group were subjected to section. All offspring of mother animals immunized with recombinant VP2+VP3 or PBS buffer suffered from thymus atrophy. The examined offspring of the group of animals injected with the 3 recombinant CAV proteins together were all found to have normal thymuses. Only 1 of the 5 examined chicks of the animals injected with recombinant VP1+VP2 was found to have a reduced thymus (Table 4). An independent experiment showed that offspring of mother animals injected with recombinant VP1 and VP3 had reduced thymuses, as described for the offspring of mother animals injected with recombinant VP2 and VP3 (Koch, results not published). Fourteen days after infection the hematocrit of all CAV infected offspring was determined. A hematocrit of 27% was selected as the limit for anemia. The offspring of the mother animals injected with PBS buffer were all found to have a strongly reduced hematocrit, with values varying between 7 and 19% (Table 5). Offspring of the mother animals injected with recombinant VP2+VP3 have a slightly higher hematocrit on average. In these groups only a single animal had a hematocrit higher than 27. An independent experiment showed that also offspring of mother animals injected with recombinant VP1 and VP3 had a reduced hematocrit (Koch, results not published). Of the 35 examined offspring of the animals injected with preparations containing VP1, VP2 and VP3 only one animal had a deviating hematocrit, whereas in the VP1+VP2 group 2 of the 29 examined animals had a hematocrit below 27%.

The high mortality was observed with offspring of mother animals injected with recombinant VP2 and VP3, 50.9% and with PBS, 48.3%. In the group of offspring of mother animals injected with recombinant VP1+VP2+VP3 the mortality is 9% and with VP1+VP2 15.4%. However, most of the animals died within 5 days after challenge. The mortality caused by a CAV infection is generally somewhat later. For this reason we have distinguished in Table 6 between mortality before day 14 and after day 14 after challenge. The mortality before day 14 is often a specific, inter alia as a result of injection. The mortality after day 14 is in the group of animals with maternal antibodies against VP1+VP2+VP3, 7%; against VP1+VP2, 0%, VP2+VP3, 27.4% and in the control group 20.7%. In the VP2+VP3 group 8 animals died after taking blood samples for determining the hematocrit as a result of the poor condition of the chicks, most probably caused by the anemia. In the PBS group 2 animals died during blood taking. All these animals had a clearly reduced thymus.

The viremia in the CAV infected offspring was examined by carrying out a virus isolation on blood cells. Heparin blood samples of 5 animals per group were taken on 6 and 14 days after challenge. The offspring of mother animals injected with VP2+VP3 or PBS, and which had practically no protection against CAV infections, were found to contain relatively high virus titers 6 and 14 days after infection. Six days after infection the offspring of animals injected with VP1+VP2+VP3 or VP1+VP2 were found to contain a clearly lower virus titer than the above-mentioned offspring. Fourteen days after infection only the group of offspring of animals injected with VP1+VP2+VP3 had a clearly lower virus titer than the other 3 groups.

The results of the induction of neutralizing antibodies in mother animals show that the recombinant CAV proteins VP1 and VP2 are very important for the induction of a neutralizing immune response. The infection experiments show that the recombinant CAV protein VP3 gives a supplementary protection in addition to the effect obtained by VP1+VP2.

The Production and Characterization of Monolonal Antibodies Against CAV

For the production of monoclonal antibodies against CAV mice were injected with crude lysates of Sf9 cells co-infected with VP1, VP2 and VP3 recombinant baculoviruses. In total, 9 different hybridoma cell lines producing monoclonal antibodies against CAV antigens were obtained.

Western blots with CAV antigens produced with the baculovirus expression system showed that the monoclonal antibodies 111.1, 111.2, 111.4, 112.1, 112.2, 120.1 and 120.2 are strongly directed against VP2 and the monoclonal antibodies 111.3 and 120.3 strongly against VP3. The monoclonal antibodies which strongly react with VP2 all show a weak cross reaction with VP3. Conversely, the monoclonal antibodies directed against VP3 show a weak cross reaction with VP2.

A serum neutralization test showed that none of the monoclonal antibodies obtained had a neutralizing activity against CAV, in spite of the fact that the sera of the immunized mice used for preparing the hybridomas did have a neutralizing activity against CAV.

In a pepscan analysis (Geysen et al., 1984) the epitope of the monoclonal antibody 111.2 was localized in the middle of VP2 (FIG. 6). The monoclonal antibody 111.3 was found to be directed against an epitope at the N terminal end of VP3 (FIG. 7), namely beside the VP3 epitope recognized by the monoclonal antibodies CVI-CAV-85.1 (FIG. 5).

Immunofluorescence showed that monoclonal antibodies directed against VP2 and VP3 recognize specific structures in CAV infected MDCC-MSB1 cells. None of the monoclonal antibodies directed against CAV antigens reacted with uninfected MDCC-MSB1 cells. The VP2-specific monoclonal antibodies recognize other structures than VP3 specific monoclonal antibodies in CAV infected cells.

Expression of VP3 in Chickcen Cells Induces Apoptosis

Jeurissen et al. have shown that CAV causes apoptosis in infected thymocytes. We have studied whether 1 of the CAV proteins, in particular VP3, is capable of independently inducing apoptosis in chicken T cells.

The coding sequences for VP3 were cloned into the expression vector pRSV-20H. The 0.46 kb BamHI-EcoRI fragment with CAV DNA sequences of positions 427–868 (Noteborn et al., 1991) were isolated from plasmid pEP-13.3. The CAV DNA fragment contains the coding sequences for VP3, and moreover 58 bp 5' and 25 bp 3'-flanking sequences. The vector pRSV-H20 was linearized with BglII, treated with CIP, and a 4.3 kb fragment was isolated. Two synthetic DNA oligomers 5'-GATCCAACCCGGGTTG-3' (SEQ ID No, 1) and 5'-AATTCAACCCGGGTTG-3' (SEQ ID NO:2) were hybridized and thus formed a double-stranded BamHI-EcoRI linker. The BamHI-EcoRI DNA linker and the 0.46 kb BamHI-EcoRI DNA fragment were ligated at the 4.3 kb BglII DNA fragment. The final construct pRSV-VP3 contained the coding region for VP3 under regulation of the Rous sarcoma virus promoter and was controlled by restriction enzyme analysis (FIG. 8*a*; Noteborn et al., 1993).

MDCC-MSB1 cells were transfected with DNA of pRSV-VP3 by means of the DEAE dextran method. Forty-two hours after transfection the cells were fixed and analyzed for VP3 expression by staining with monoclonal CVI-CAV-85.1. The cells were also stained with propidium iodide which very strongly stains DNA of intact nuclei but weakly DNA of apoptotic nuclei (Telford et al., 1992). More than 90% of the transfected cells contained a fine-granular distribution of VP3 in the nucleus which was stained by propidium iodide. Two days after infection 40% of the cells expressing VP3 were found to contain nuclei which were weakly stained with propidium iodide, and VP3 was present as aggregates. Three days and later after infection more than 90% of the VP3 containing cells were found to contain VP3 aggregates and DNA which very weakly stained with propidium iodide (FIG. 9). Three days after transfection the DNA of the VP3 transfected cells showed the oligonucleosomal ladder pattern characteristic of apoptosis.

The VP3 distribution observed in transfected cells fully corresponds with that in CAV-infected MDCC-MSB1 cells. Early after infection (after 1–1.5 day) VP3 is fine-granularly distributed in the nucleus: the cellular DNA is still intact at this stage. Late in infection (after approximately three days) VP3 forms aggregates in the nucleus (Koch, date not published). The DNA of the CAV-infected cells is fragmented (Jeurissen et al., 1992).

Our conclusion is that VP3 in itself is capable of inducing the CAV-specific apoptosis in MDCC-MSB1 cells. Expression of pRSV-VP3 DNA coding for VP3 in the monocyte cell line LSCC-HD11 also led to apoptosis in these cells.

Expression of the VP2 protein in MDCC-MSB1 cells also leads to damage to the cellular DNA. Three days after infection of MDCC-MSB1 cells with DNA coding for VP2, in 20% and after 5 days, in approximately half of the transfected cells the nuclei are weakly stained with propidium iodide. Therefore, also VP2, though in a lesser degree than VP3, seems involved in the induction of the CAV-specific cell death.

The Effect of Truncated VP3 on the Induction of Apoptosis in MDCC-MSB1 Cell

VP3 is a protein of 121 amino acids in length, contains two proline-rich pieces, a hydrophobic region and two strongly positively-charged portions (FIG. 8b (SEQ ID NO:7)). The positively charged regions are possibly nucleus localization signals and/or DNA-binding domains (Noteborn et al. 1987; Ramakrishnan, 1993).

We have studied whether the basic C terminal end of VP3 is involved in the apoptotic activity of VP3. To this end, a truncated VP3 product was made by deletion of 11 codons at the C terminus'of the VP3-coding sequences. Plasmid pEP-VP3 was cut with the restriction enzymes BamHI and HindIII, and the 0.38 kb BamHI-HindIII DNA was isolated. Two synthetic DNA oligomers, 5'-AGCTTGATTACCACTACTCCCTGAG-3' (SEQ ID NO:28) and 5'-TCGACTCAGGGAGTAGTGGTAATCA-3' (SEQ ID NO:27), were hybridizied and thus formed together the double-stranded HindIII-SalI DNA linker. Plasmid pRSV-H20 was cut with BglII and SalI, treated with alkaline phosphatase, and a 4.3 kb DNA fragment was isolated. The HindIII-SalI DNA linker and the 0.38 kb BamHI-HindIII fragment were ligated in the 4.3 kb BglII-SalI fragment. The final construct pRSV-tr containing the coding sequences for the truncated VP3 protein under the regulation of the RSV promoter (FIG. 8a) was analyzed by means of restriction enzyme and sequence analysis.

MDCC-MSB1 cells were transiently transfected with pRSV-tr DNA and, at different moments after transfection, stained with monoclonal CVI-CAV-85.1 and propidium iodide. Immunofluorescence showed that 42 hours after transfection most of the cells expressing truncated VP3 contained fine-granular VP3 in their nuclei. The cellular DNA was strongly stained with propidium iodide. Three days after transfection still 80% of the cells expressing truncated VP3 had nuclei which strongly stained with propidium iodide (FIG. 9). DNA isolated from MDCC-MSB1 cells on 3 days after transfection with pRSV-tr was found to be much less degraded than DNA isolated from pRSV-VP3-transfected MDCC-MSB1 cells. The fraction of the propidium iodide positive nuclei of cells expressing truncated VP3 slowly declined to approximately 50% on 5 days after transfection. Most of the cells containing truncated VP3 and weakly stained by prosidium iodide had a granular VP3 distribution. Only a single cell contained VP3 aggregates.

The expression of truncated VP3 in MDCC-MSB1 cells apparently induces cell death much less efficiently than expression of wild type VP3. It is also remarkable that the VP3 mutant can form much fewer aggregates than wild type VP3.

Expression of VP3 in Human Tumor Cells Induces Apoptosis

For the expression of VP3 in human cells the expression vectors pRSV-VP3 (FIG. 8a) and pCMV-VP3 were used. The coding sequences for VP3 were cloned into the expression vector pCMV-neo containing the strong promoter of the cytomegalovirus (CMV) immediate early gene (Boshart et al., 1985). The 0.46 BamHI fragment with CAV DNA sequences of positions 427–868 (Noteborn et al., 1991) were isolated from plasmid pAc-VP3 (FIG. 4). The vector pCEfv-neo was linearized with BamHI, treated with CIP, and a 7.5 kb fragment was isolated. The 0.46 BamHI DNA fragment was ligated at the 7.5 BamHI DNA fragment. The right orientation of the VP3-coding sequence with respect to the CMV promoter in the final construct pCMV-VP3 was determined by means of restriction enzyme analysis (FIG. 10).

For the expression of truncated VP3 in human cells the 0.46 kb XhoI-SalI fragment of plasmid pRSV-tr coding for truncated VP3 (FIG. 8a) was provided with blunt ends by treatment with Klenow polymerase and isolated. The vector pCMV-neo was linearized with BamHI, provided with blunt ends and dephosphorylated by treatment with CIP. The 0.46 kb blunt end DNA fragment was ligated at the 7.5 blunt end DNA fragment. The construct pcMV-tr contains the coding sequences for truncated VP3 under regulation of the CMV promoter (FIG. 10).

In the first instance, VP3 was expressed in the 3 human hematopoietic tumor cell lines KG-1, DOHH-2 and K562, and in an immortalized cell line, Jobo-0. The cell lines KG-1 and K562 have been derived from different patients with human myeloid leukemia (Koeffler and Golde 1980) and DOHH-2 from a patent with a follicular B-lymphoma (Landegent et al., results not published). Jobo-0 cells were immortalized with the Epstein Barr Virus (Landegent, results not published). The 4 human cell lines were transfected with DNA of pRSV-VP3 (KG-1) or with DNA of pCMV-VP3 (DOHH-2, K562 and Jobo-1). The cells were fixed and analyzd for VP3 expression by staining with monclonal CVI-CAV-85.1 and induction of apoptosis by staining with propidium iodide. Early after transfection VP3 positive cells were observed with a fine-granular distribution of VP3 in the nucleus which was stained with propidium iodide and VP3 positive cells with nuclei containing VP3 aggregates with nuclei that did not stain with propidium iodide. The percentage of VP3 positive cells with nuclei that did not stain with propidium iodide and contained VP3 aggregates was found for the 4 different hematopoietic cell lines to range between 75 and 95% 5 days after transfection (FIG. 11a). Then K562 cells were transfected with DNA of the plasmid pCMV-tr which expresses C terminal truncated VP3. Expression of truncated VP3 in K562 cells induced the cell death much less efficiently than wild type VP3.

Our conclusion is that expression of VP3 in human hematopoietic tumor cells leads to specific induction of apoptosis. Expression of VP3 in the human breast tumor cell line MCF-7 (Lippmann et al. 1980) also resulted in the induction of apoptosis (Noteborn et al., results not published).

In the literature it is described that (human) tumors and tumor cell lines that do not contain functional p53 are less/not susceptible to induction of cell death by chemotherapeutics and radiation treatment (Lowe et al., 1993). The tumor suppressor gene p53 acts as intermediary in the induction of apoptosis by specific anti-tumor agents. We have examined whether VP3 is capable of inducing apoptosis in human cells that do not possess p53 or possess mutated p53, VP3 was expressed in human osteosarcoma cells by means of DEAE-dextran transfection with plasmid pCMV-VP3. The osteosarcoma-derived Saos-2 cells cannot synthesize p53, and Saos-2/alal43 cells express mutated and thus non-functional p53. As a positive control the U2-OS cell line containing wild type p53 was used (Diller et al., 1990). The results given in FIG. 12a show that VP3 can induce apoptosis in a comparable degree in cells that are p53$^-$ (Saos-2 and Saos-2/Alal43) or p53$^+$ (U2-OS). Six days after transfection most of the VP3 positive cells are apoptotic. Expression of truncated VP3 induced much less efficient apoptosis in Saos-2 cells (FIG. 12b). Our conclusion is that VP3 can specifically induce apoptosis in human tumor cells containing or not containing the tumor suppressor gene p53.

DESCRIPTION OF THE FIGURES

FIG. 1 (SEQ ID NOS:3 and 4) gives the DNA sequence and the amino acid sequence of the VP1 protein of Chicken Anemia Virus. The numbering of the CAV DNA sequences is as given in Dutch patent no. 9002008.

FIG. 2 (SEQ ID NOS:5 and 6) gives the DNA sequence and the amino acid sequence of the VP2 protein of Chicken Anemia Virus. The numbering of the CAV DNA sequences is as given in Dutch patent no. 9002008.

FIG. 3 (SEQ ID NOS:7 and 8) gives the DNA sequence and the amino acid sequence of the VP3 protein of Chicken Anemia Virus, The numbering of the CAV DNA sequences is as given in Dutch patent no. 9002008.

FIG. 11b shows the kinetics of the apoptotic effect of VP3 (—○—) or truncated VP3 (—●—). Per experiment at least 200 cells were counted.

FIG. 12b shows the kinetics of the apoptotic effect of VP3 (—○—) or truncated VP3 (—●—). The percentages of the VP3-positive cells with nuclei that weakly stain with propidium iodide, apoptotic cells, are given. Per experiment at least 500 cells were counted.

REFERENCES

Figure 4:
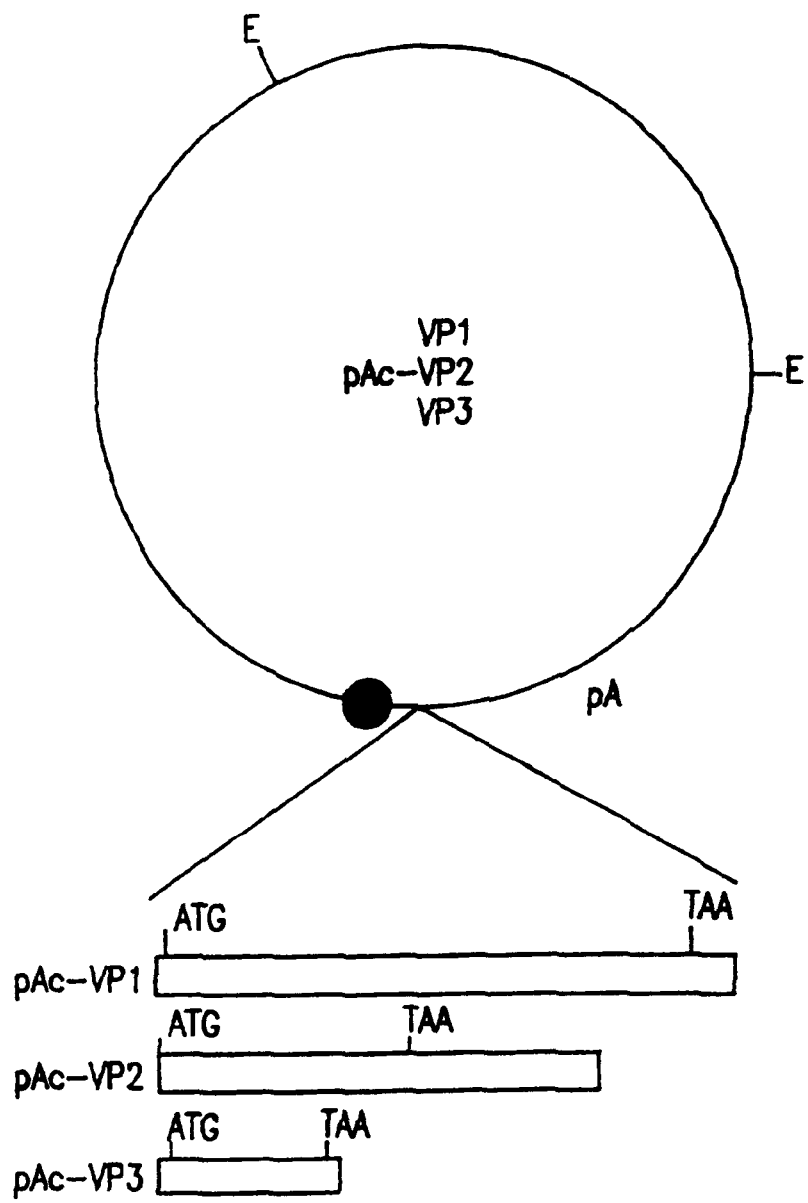
FIG. 4 shows the diagrammatic representation of the 3 CAV recombinant transfer vectors pAc-VP1, pAc-VP2 and pAc-VP3 ●=polyhedron promoter, ATG=initiation codon, TAA=stop codon, pA=polyadenylation signal, E=EcoRI.
Figure 5:
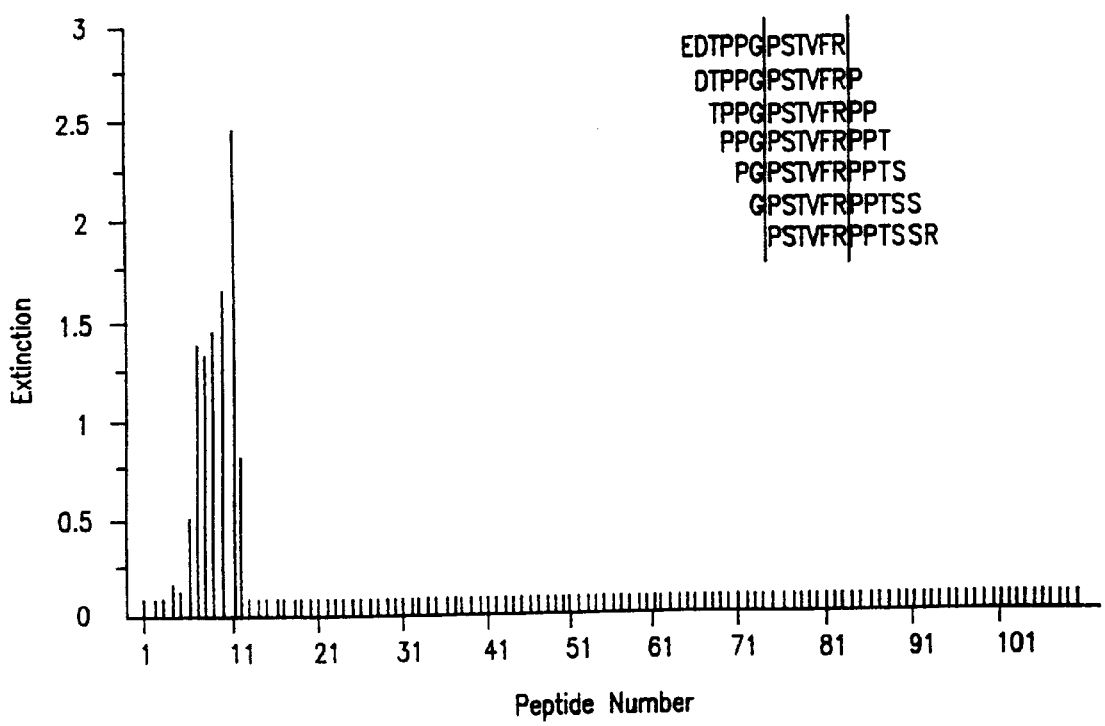
FIG. 5 (SEQ ID NOS: 9–15) shows the pepscan analysis of the monoclonal antibody CVI-CAV-85.1 with peptides (12-mers) derived from VP3. The core sequence PSTVFR, (SEQ ID NO:30) against which the monoclonal CVI-CAV-85.1 is directed, is at positions 12 to 17 of the VP3 amino acid sequence (Noteborn et al., 1991).
Figure 6:
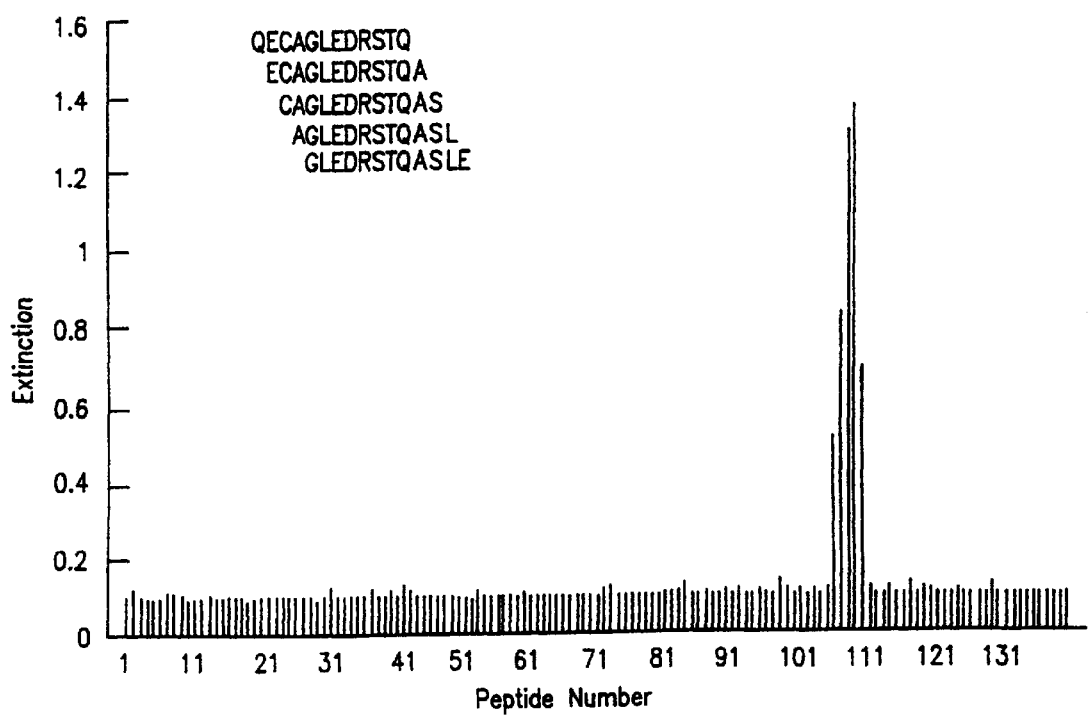
FIG. 6 (SEQ ID NOS:16–20) shows the pepscan analysis of the monoclonal antibody 111.2 with peptides (12-mers) derived from VP2. Monoclonal 111.2 is directed against the epitope GLEDRSTQ (SEQ ID NO:31) which is at positions 109 to 116 of the VP2 amino acid sequence (Noteborn et al., 1991). Only the results obtained with peptides nos. 1 through 140 are shown (extinction of peptides nos. 141 through 206≦0.103).
Figure 7:
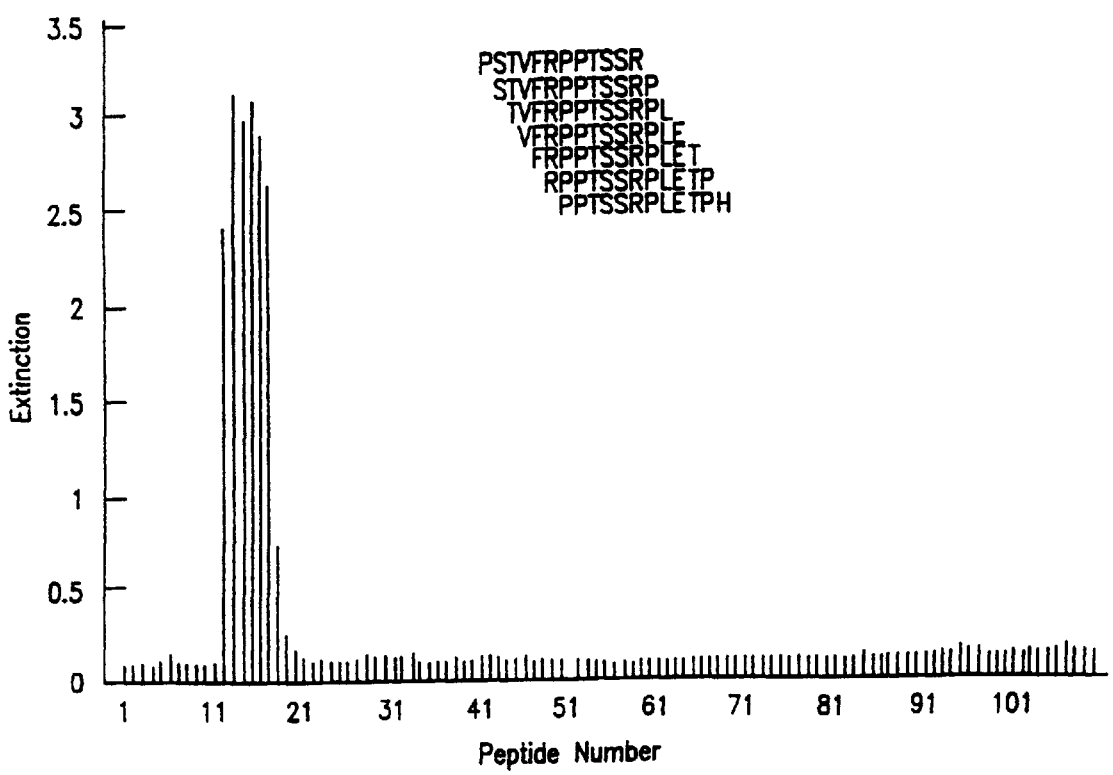
FIG. 7 (SEQ ID NOS:21–27) shows the pepscan analysis of the monoclonal antibody 111.3 with peptides (12-mers) derived from VP3. Monoclonal 111.3 is directed against the epitope PTSSR (SEQ ID NO:32) which is at positions 19 to 23 of the VP3 amino acid sequence (Noteborn et al., 1991).
Figures 8A, 8B:
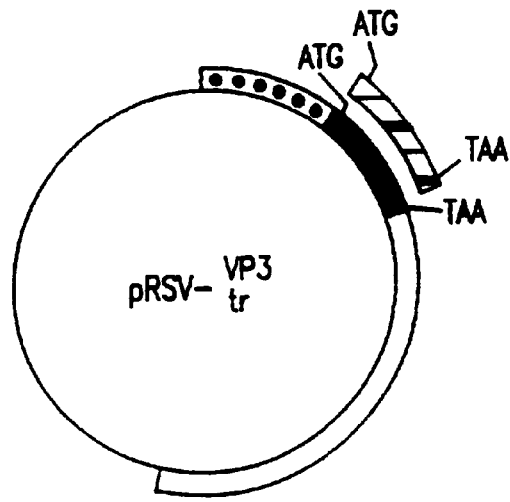
FIGS. 8A-8B. Panel A shows the diagrammatic representation of the 2 expression vectors pRSV-VP3 and pRSV-tr ■=VP3 coding sequence, ▨=VP3-tr coding sequence, ⊡=RSV LTR coding sequence, □=SV40 coding sequence. Panel B (SEQ ID NO:1) shows the amino acid sequence of the CAV protein VP3. The proline residues are printed in italics and the basic amino acids in heavy type. The 11 C terminal amino acids, the codons of which are deleted in the expression vector, are underlined.
Figure 9:
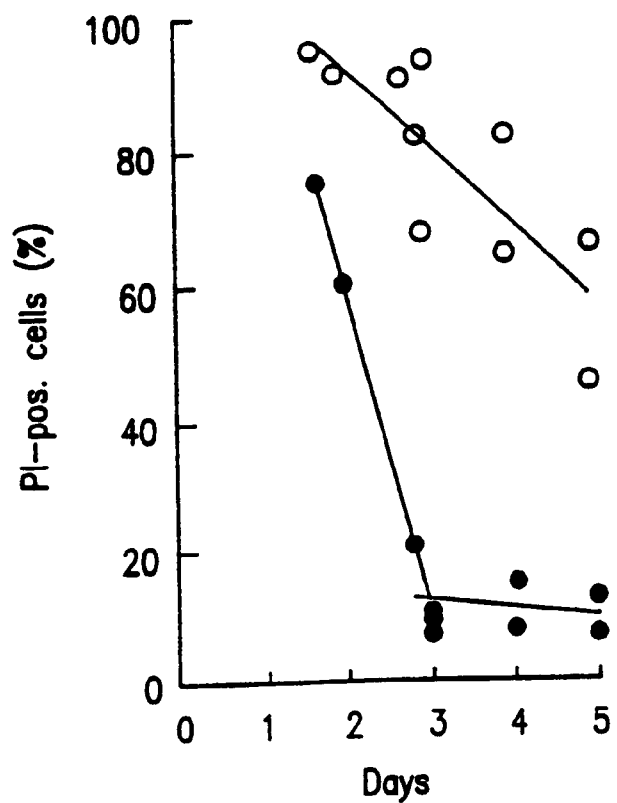
FIG. 9 shows the kinetics of the apoptotic effect of VP3 or truncated VP3. MDCC-MSB1 cells were transfected with plasmid PRSV-VP3 (●) or PRSV-tr (○), fixed and stained with the monoclonal antibody CVI-CAV-85.1 at different times after transfection. The percentages of the immunofluorescent cells with nuclei which normally stain with propidium iodide are given. Per experiment at least 100 cells were counted which had expressed VP3 or truncated VP3.
Figure 10:
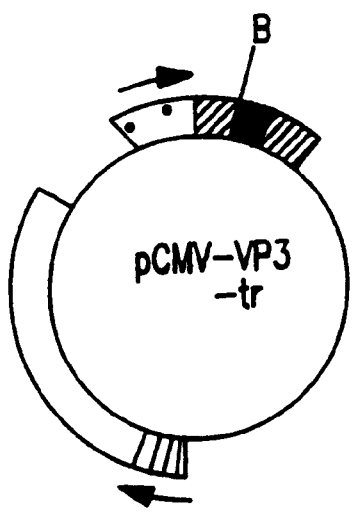
FIG. 10 shows the diagrammatic representation of the expression vectors pCMV-VP3 and pCMV-tr ⊡=CMV promoter, ▨=rabbit B-globin, □=neomycin resistance, ■=VP3 or truncated VP3, ⊞=RSV promoter, —=pBR322 sequences, B=BamHI cloning sites.
Figure 11A:
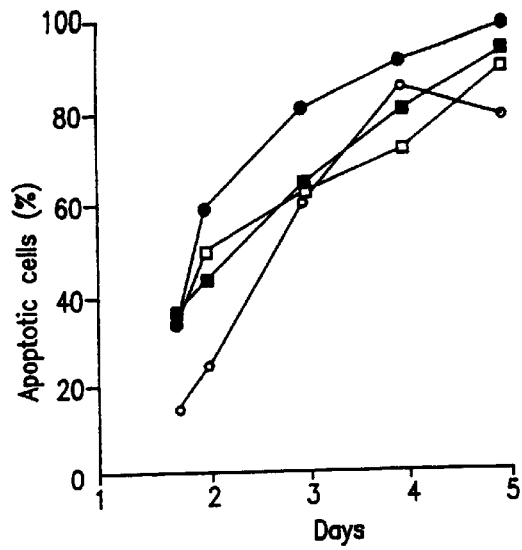
FIGS. 11A–11B shows the kinetics of the apoptotic effect of VP3 on human hematopoietic (tumor) cells. The cell line KG1 (—○—) was transfected with plasmid pRSV-VP3, and the cell lines DOHH-2, (—●—) K562 (—□—), and Jobo-0 (—■—), were transfected with plasmid pCMV-VP3. The percentages of the VP3-positive cells with nuclei that weakly stain with propidium iodide, apoptotic cells, are given.
Figure 11B:
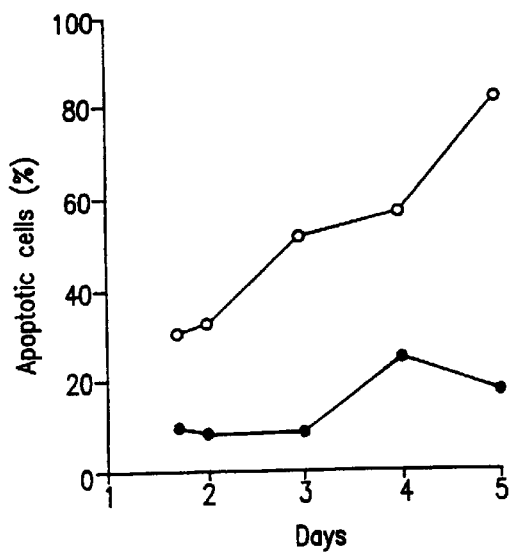
Figure 12A:
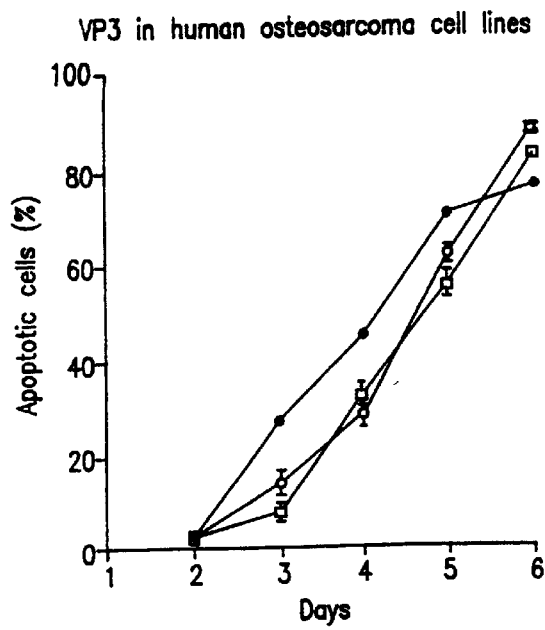
FIGS. 12A–12B shows the kinetics of the apoptotic effect of VP3 on human osteosarcoma cell lines. Cells of the cell lines Saos-2(—○—), Saos-2/Alal43 (—□—) and U2-OS (—●—) were transfected with plasmid pCMV-VP3.
Figure 12B:
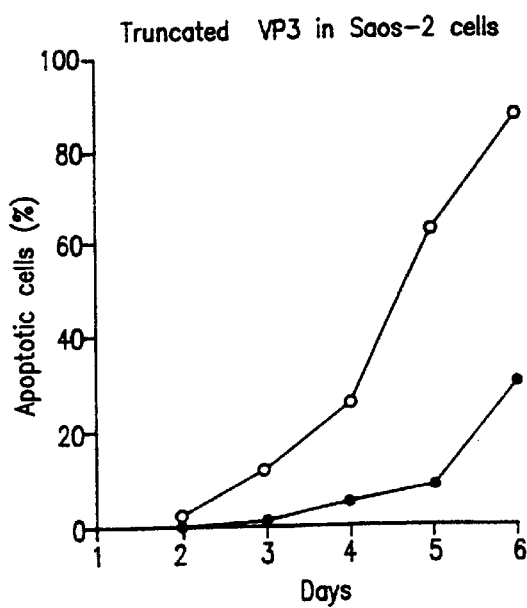

1. Bishop, D. H. L., Hill-Perkins, M., Jones, I. M., Kitts, P. A., Lopez-Ferber, M., Clarke, A. T., Possee, R. D., Pullen, J., and Weyer, U. 1992. Construction of baculovirus expression vectors in vivo and in cultured insect cells. In: Baculovirus and recombinant protein production processes 1992. Eds. Vlak, J., Schlaeger E. J., and Bernard, A. R. Editiones Roche, F. Hoffmann-La Roche Ltd., Basel, Switzerland.
2. Boss, M. A., Kenten, J. H., Entage, J. S. and Wood, C. R. 1984. EP 0120694.
3. Brown, C. S., Van Lent, W. M., Vlak, J. M., and Spaan, W. J. M. 1991. Assembly of empty capsids by using baculovirus recombinants expressing human parvovirus B19 structural proteins. Journal of Virology 65, 2702–2706.
4. Brown, M., and Faulkner, P. 1977. A plaque assay for nuclear polyhedrosis viruses using a solid overlay. Journal of General virology 36, 361–364.

5. Cabilly, S., Holmes, W. E., Wetzel, R. B., Heyneker, H. L. and Riggs, A. D. 1984. EP 0125023.
6. Chettle, N. J., Eddy, R. K., Saunders, J., Wyeth, P. J. 1991. A comparison of serum neutralisation, immunofluorescence and immunoperoxidase tests for the detection of antibodies to chicken anaemia agent. The Veterinary Record 128, 304–306.
7. De Boer, G. F., Jeurisssen, S. H. M., Noteborn, M. H. M., and Koch, G. 1992. Biological aspects of Marek's disease virus infections as related to dual infections with chicken anemia. Volume 1, p 262–271. In: Proceedings World's Poultry Congres Symposium, Amsterdam, The Netherlands.
8. Engstrom, B. E. 1988. Blue wing disease of chickens: isolation of avian reovirus and chicken anaemia agent. Avian Pathology 17, 23–32.
9. Gelderblom, H., Kling, S., Lurz, R., Tischer, I., and Von Bülow, V. 1989. Morphological characterization of chicken anaemia agent (CAA). Archives of Virology 109, 115–120.
10. Geysen, H. M., Barteling, S. J., and Meloen, R. 1985. Small peptides induce antibodies with a sequence and structural requirement for binding antigen comparable to antibodies raised against the native protein. Proceedings of National Academy of Sciences USA 82, 178–182.
11. Goryo, M., Sugimura, H., Matsumoto, S., Umemura, T., and Itakura, C. 1985. Isolation of an agent inducing chicken anemia. Avian Pathology 14, 483–496.
12. Graham, F. L., and Van der Eb, A. J. 1973. A new technique for the assay of infectivity of human adenovirus 5 DNA. Virology 52, 456–467.
13. Jeurissen, S. H. M., Janse, M. E., Van Roozelaar, D. J., Koch, G., and De Boer, G. F. 1992a. Susceptibility of thymocytes for infection by chicken anemia virus is related to pre and post hatching development. Developmental Immunology 2, 123–129.
14. Jeurissen, S. H. M., Janse, E. M., Ekino, S., Nieuwenhuis, P., Koch, G., and De Boer, G. F. (1988). Monoclonal antibodies as probes for defining cellular subsets in the bone marrow, thymus, bursa of Fabricius, and spleen of the chicken. Veterinary Immunology and Immunopathology 19, 225–238.
15. Jeurissen, S. H. M., Pol, J. M. A., and De Boer, G. F. 1989. Transient depletion of cortical thymocytes induced by chicken anaemia agent. Thymus 14, 115–123.
16. Jeurissen, S. H. M., Wagenaar, F., Pol, J. M. A., Van der Eb, A. J., and Noteborn, M. H. M. 1992b. Chicken anemia virus causes apoptosis of thymocytes after in vivo infection and of cell lines after in vitro infection. Journal of Virology 66, 7383–7388.
17. Laemmli, U. K. 1970. Cleavage of structural proteins during the assembly of the head of bacteriophage T4. Nature, 227, 680–685.
18. Lucio, B. K., Schat, K. A., and Shivaprasad, H. L. 1990. Identification of the chicken anemia agent, reproduction of the disease, and serological survey in the United States. Avian Diseases 34, 146–153.
19, Maniatis, T., Fritsch, E. F., and Sambrook, J. 1982. Molecular Cloning: A Laboratory Manual. New York: Cold Spring Harbor Laboratory.
20. Matsuura, Y., Possee, R. D., Overton, H. A., and Bishop, D. H. L. 1987. Baculovirus expression vector requirements for high level expression of proteins, including glycoproteins. Journal of General Virology: 68, 1233–1250.
21. McIlroy, S. G., McNulty, M. S., Bruce, D. W., Smyth, J. A., Goodall, E. A., and Alcorn, M. J. 1992. Economic effects of clinical chicken anemia agent infection on profitable broiler production. Avian Diseases 36, 566–574.
22. McNulty, M. S., Connor, T. J., McNeilly, F., McLoughlin, M. F., and Kirkpatrick, K. S. 1990. Preliminary characterization of isolates of chicken anemia agent from the United Kingdom. Avian Pathology 19, 67–73.
23. McNulty, M. S., Connor, T. J., McNeilly, F., and Spackman, D. 1989. Chicken anemia agent in the United States: isolation of the virus and detection of antibody in the broiler breeder flocks. Avian Diseases 33, 691–694.
24. McNulty, M. S., McIlroy, S. G., Bruce, D. W., and Todd, D. 1991. Economic effects of subclinical chicken anemia agent in broiler chickens. Avian Diseases 35, 263–268.
25. Noteborn, M. H. M., en De Boer, G. F. 1990. Nederlands Octrooi, Nr. 9002008.
26. Noteborn, M. H. M., De Boer, G. F., Van Roozelaar, D. J., Karreman, C., Kranenburg, O., Vos, J. G., Jeurissen, S. R. M., Hoeben, R. C., Zantema, A., Koch, G., Van Ormondt, H., and Van der Eb, A. J. 1991. Characterization of cloned chicken anemia virus DNA that contains all elements for the infectious replication cycle. Journal of Virology 65, 3131–3139.
27. Noteborn, M. H. M., Kranenburg, O., Zantema, A., Koch. G., De Boer, G. F., and Van der Eb, A. J. (1992a). Transcription of the chicken anemia virus (CAV) genome and synthesis of its 52-kDa protein. Gene 118, 267–271.
28. Noteborn, M. H. M., Van der Eb, A. J., Koch, G., and Jeurissen, S. H. M. (1993). VP3 of chicken anemia virus (CAV) causes apoptosis. In: Vaccines'93. CSHL Press. Cold Spring Harbor, USA. P. 299–304
29. Noteborn, M. H. M., Verschueren, C. A. J., Van Roozelaar, D. J., Veldkamp, S., Van der Eb, A. J., De Boer, G. F. 1992b. Detection of chicken anemia virus by DNA hybridization and polymerase chain reaction. Avian Pathology 21, 107–118.
30. Offringa, R., Gebel, S., Van Dam, H., Timmers, M., Smits, A., Zwart, R., Stein, B., Bos, J. L., Van der Eb, A. J., and Herrlich, P. 1990. A novel function of the transforming domain of E1A: repression of AP-1 activity. Cell 62. 527–538.
31. Ramakrishnan, V., Finch, J. T., Graziano, V., Lee, P. L. and Sweet, R. M. 1993. Crystal structure of globular domain of histone H5 and its implications for nucleosome binding. Nature 362: 219–223.
32. Rosenberger, J. K., and Cloud, S. S. 1989. The isolation and characterization of chicken anemia agent (CAA) from broilers in the United States. Avian Diseases 33, 707–713.
33. Smith, G. E., and Summers, M. D., and Fraser, M. J. 1983. Production of human beta interferon in insect cells infected with a baculovirus expression vector. Molecular and Cellular Biology 3, 2156–2165.
34. Summers, M. D., and Smith, G. E. 1987. A Manual of Methods for Baculovirus Vectors and Insect Cell Culture Procedures. Texas Agricultural Experiment Station Bulletin No. 1555.
35. Telford, W. G., King, L. E., and Fraker, P. J. 1992. Comparitive evaluation of several DNA binding dyes in the detection of apoptosis-asssociated chromatin degradation by flow cytometry. Cytometry: 13: 137–143.
36. Todd, D., Creelan, J. L., Mackie, D. P., Rixon, F., and McNulty, M. S. 1990. Purification and biochemical characterisation of chicken anaemia agent. Journal of General Virology 71, 819–823.
37. Todd, D., Niagro, F. D., Ritchie, B. W., Curran, W., Allan, G. M., Lukert, P. D., Latimer, K. S., Steffens III, W. L., and McNulty, M. S. 1991. Comparison of three animal viruses with circular single-stranded DNA genomes. Archives of Virology 117, 129–135.
38. Todd, D., Mawhinney, K. A., and McNulty, M. S. 1992. Detection and differentiation of chicken anemia virus isolates by using the polymerase chain reaction. Journal of Clinical Microbiology 30, 1661–1666.
39. Von Bülow, V., Fuchs, B., and Bertram, M. 1985. Untersuchun gen über den Erreger der Infektiösen Anämie bei Hühnerkücken (CAA) in vitro: Vermehrung, Titration, Serumneutralisationstest und indirekter Immunofluoreszenstest. Journal of-Veterinary Medicine B 32, 679–693.
40. Von Bülow, V., Fuchs, B., Vielitz, B., and Landgraf, H. 1983. Frühsterblichkeitssyndrom bei Küken nacb Doppelinfektior mit dem Virus des Marekschen Krankheit (MDV) und einen Anämie-Erreger (CAA). Journal of Veterinary Medicine B 30, 742–750.
41. Von Bülow, V., Rudolph, R., and Fuchs, B. 1986. Folgen der Doppelinfektion von Küken mit Adenovirus oder Reovirus und dem Erreger der aviären infektiosen Anämie (CAA). Journal of Veterinary Medicine B 33, 717–726.
42. Winter, G. P. 1987. EP 239400.
43. Winter, G. P., Gussow, D. and Ward, E. S. 1990. Europese octrooiaanvrage No. 0368684.
44. Yuasa, N. 1983. Propagation and infectivity titration of the Gifu-1 strain of chicken anaemia agent in a cell line (MDCC-MSB1) derived from Marek's disease lymphoma. National Institute Animal Health Quaterly 23, 13–20.
45. Yuasa, N., Taniguchi, T., Goda, M., Shibatanni, M., Imada, T., and Hihara, H. 1983. Isolation of chicken anemia agert with MDCC-MSB1 cells from chickens in the field. National Institute Animal Health Quaterly 23, 78–81.
46. Yuasa, N., Taniguchi, T., and Yoshida, I., 1979. Isolation and some properties of an agent inducing anaemia in chicks. Avian Diseases 23, 366–385.
47. Yuasa, N., Taniguchi, and Yoshida, I. 1980. Effect of infectious bursal disease virus infection on incidence of anaemia by chicken anaemia agent. Avian Diseases 24. 202–209.

We claim:

1. A composition for generating antibodies against a Chicken Anemia Virus ("CAV"), said composition comprising:

a first polypeptide comprising an amino acid sequence depicted in SEQ ID NO: 5, a second polypeptide comprising an amino acid sequence depicted in SEQ ID NO: 3, and an adjuvant in an amount sufficient to generate antibodies against a CAV when said composition is introduced into an animal.

2. The composition according to claim 1, wherein said antibodies are neutralizing antibodies.

3. The composition according to claim 1, wherein said animal is a chicken.

4. The composition according to claim 3, wherein said animal is a mouse.

5. A method of generating antibodies against a Chicken Anemia Virus ("CAV") polypeptide, said method comprising:

providing an animal with a sufficient amount of a composition which elicits an immune response in said animal, wherein said composition comprises a first polypeptide comprising an amino acid sequence depicted in SEQ ID NO: 5, and a second polypeptide comprising an amino acid sequence depicted in SEQ ID NO: 3, whereby antibodies against said CAV polypeptide are generated.

6. The method according to claim 5, wherein said composition further comprises an adjuvant.

7. The method according to claim 5, wherein said animal is a chicken.

8. The method according to claim 5, wherein said animal is a mouse.

* * * * *

```
                       SEQUENCE LISTING (1) GENERAL INFORMATION:

(iii) NUMBER OF SEQUENCES: 32

(2) INFORMATION FOR SEQ ID NO: 1:

(i) SEQUENCE CHARACTERISTICS:
        (A) LENGTH: 16 base pairs
        (B) TYPE: nucleic acid
        (C) STRANDEDNESS: unknown
        (D) TOPOLOGY: unknown (ii) MOLECULE TYPE: DNA (genomic)

(iii) HYPOTHETICAL: NO (xi) SEQUENCE DESCRIPTION: SEQ ID NO: 1:

GATCCAACCC GGGTTG                                                          16

(2) INFORMATION FOR SEQ ID NO: 2:

(i) SEQUENCE CHARACTERISTICS:
        (A) LENGTH: 16 base pairs
        (B) TYPE: nucleic acid
        (C) STRANDEDNESS: unknown
        (D) TOPOLOGY: unknown (ii) MOLECULE TYPE: DNA (genomic)

(iii) HYPOTHETICAL: NO (xi) SEQUENCE DESCRIPTION: SEQ ID NO: 2:

AATTCAACCC GGGTTG                                                          16

(2) INFORMATION FOR SEQ ID NO: 3:

(i) SEQUENCE CHARACTERISTICS:
        (A) LENGTH: 449 amino acids
        (B) TYPE: amino acid
        (D) TOPOLOGY: unknown (ii) MOLECULE TYPE: protein
```

(iii) HYPOTHETICAL: NO (xi) SEQUENCE DESCRIPTION: SEQ ID NO: 3:

```
Met Ala Arg Arg Ala Arg Arg Pro Arg Gly Arg Phe Tyr Ser Phe Arg
 1               5                  10                  15

Arg Gly Arg Trp His His Leu Lys Arg Leu Arg Arg Arg Tyr Lys Phe
                20                  25                  30

Arg His Arg Arg Arg Gln Arg Tyr Arg Arg Arg Ala Phe Arg Lys Ala
             35                  40                  45

Phe His Asn Pro Arg Pro Gly Thr Tyr Ser Val Arg Leu Pro Asn Pro
         50                  55                  60

Gln Ser Thr Met Thr Ile Arg Phe Gln Gly Val Ile Phe Leu Thr Glu
 65                  70                  75                  80

Gly Leu Ile Leu Pro Lys Asn Ser Thr Ala Gly Gly Tyr Ala Asp His
                 85                  90                  95

Met Tyr Gly Ala Arg Val Ala Lys Ile Ser Val Asn Leu Lys Glu Phe
                100                 105                 110

Leu Leu Ala Ser Met Asn Leu Thr Tyr Val Ser Lys Ile Gly Gly Pro
            115                 120                 125

Thr Ala Gly Glu Leu Ile Ala Asp Gly Ser Lys Ser Gln Ala Ala Asp
130                 135                 140

Asn Trp Pro Asn Cys Trp Leu Pro Leu Asp Asn Asn Val Pro Ser Ala
145                 150                 155                 160

Thr Pro Ser Ala Trp Trp Arg Trp Ala Leu Met Met Met Gln Pro Thr
                165                 170                 175

Asp Ser Cys Arg Phe Phe Asn His Pro Lys Gln Met Thr Leu Gln Asp
            180                 185                 190

Met Gly Arg Met Phe Gly Gly Trp His Leu Phe Arg His Ile Glu Thr
        195                 200                 205

Arg Phe Gln Leu Leu Ala Thr Lys Asn Glu Gly Ser Phe Ser Pro Val
    210                 215                 220

Ala Ser Leu Leu Ser Gln Gly Glu Tyr Leu Thr Arg Arg Asp Asp Val
225                 230                 235                 240

Lys Tyr Ser Ser Asp His Gln Asn Arg Trp Gln Lys Gly Gly Gln Pro
                245                 250                 255

Met Thr Gly Gly Ile Ala Tyr Ala Thr Gly Lys Met Arg Pro Asp Glu
            260                 265                 270

Gln Gln Tyr Pro Ala Met Pro Pro Asp Pro Pro Ile Ile Thr Ala Thr
        275                 280                 285

Thr Ala Gln Gly Thr Gln Val Arg Cys Met Asn Ser Thr Gln Ala Trp
    290                 295                 300

Trp Ser Trp Asp Thr Tyr Met Ser Phe Ala Thr Leu Thr Ala Leu Gly
305                 310                 315                 320

Ala Gln Trp Ser Phe Pro Pro Gly Gln Arg Ser Val Ser Arg Arg Ser
                325                 330                 335

Phe Asn His His Lys Ala Arg Gly Ala Gly Asp Pro Lys Gly Gln Arg
            340                 345                 350

Trp His Thr Leu Val Pro Leu Gly Thr Glu Thr Ile Thr Asp Ser Tyr
        355                 360                 365

Met Ser Ala Pro Ala Ser Glu Leu Asp Thr Asn Phe Phe Thr Leu Tyr
    370                 375                 380

Val Ala Gln Gly Thr Asn Lys Ser Gln Gly Tyr Lys Phe Gly Thr Ala
385                 390                 395                 400
```

```
Thr Tyr Ala Leu Lys Glu Pro Val Met Lys Ser Asp Ala Trp Ala Val
                405                 410                 415

Val Arg Val Gln Ser Val Trp Gln Leu Gly Asn Arg Gln Arg Pro Tyr
            420                 425                 430

Pro Asn Asp Val Asn Trp Ala Asn Ser Thr Met Tyr Trp Gly Thr Gln
        435                 440                 445

Pro
```

(2) INFORMATION FOR SEQ ID NO: 4:

(i) SEQUENCE CHARACTERISTICS:
        (A) LENGTH: 1348 base pairs
        (B) TYPE: nucleic acid
        (C) STRANDEDNESS: unknown
        (D) TOPOLOGY: unknown (ii) MOLECULE TYPE: DNA (genomic)

(iii) HYPOTHETICAL: NO (xi) SEQUENCE DESCRIPTION: SEQ ID NO: 4:

```
ATGGCAAGAC GAGCTCGCAG ACCGAGGCCG ATTTTACTCC TTCAGAAGAG GACGGTGGCA      60

CCACCTCAAG CGACTTCGAC GAAGATATAA ATTTCGACAT CGGAGGAGAC AGCGGTATCG     120

TAGACGAGCT TTTAGGAAGG CCTTTCACAA CCCCCGCCCC GGTACGTATA GTGTGAGGCT     180

GCCGAACCCC CAATCTACTA TGACTATCCG CTTCCAAGGG GTCATCTTTC TCACGGAAGG     240

ACTCATTCTG CCTAAAAACA GCACAGCGGG GGGCTATGCA GACCACATGT ACGGGGCGAG     300

AGTCGCCAAG ATCTCTGTGA ACCTGAAAGA GTTCCTGCTA GCCTCAATGA ACCTGACATA     360

CGTGAGCAAA ATCGGAGGCC CCATCGCCGG TGAGTTGATT GCGGACGGGT CTAAATCACA     420

AGCCGCGGAC AATTGGCCTA ATTGCTGGCT GCCGCTAGAT AATAACGTGC CCTCCGCTAC     480

ACCATCGGCA TGGTGGAGAT GGGCCTTAAT GATGATGCAG CCCACGGACT CTTGCCGGTT     540

CTTTAATCAC CCAAAGCAGA TGACCCTGCA AGACATGGGT CGCATGTTTG GGGCTGGCA     600

CCTGTTCCGA CACATTGAAA CCCGCTTTCA GCTCCTTGCC ACTAAGAATG AGGGATCCTT     660

CAGCCCCGTG GCGAGTCTTC TCTCCCAGGG AGAGTACCTC ACGCGTCGCG ACGATGTTAA     720

GTACAGCAGC GATCACCAGA ACCGGTGGCA AAAAGGCGGA CAACCGATGA CGGGGGGCAT     780

TGCTTATGCG ACCGGGAAAA TGAGACCCGA CGAGCAACAG TACCCTGCTA TGCCCCCAGA     840

CCCCCCGATC ATCACCGCTA CTACAGCGCA AGGCACGCAA GTCCGCTGCA TGAATAGCAC     900

GCAAGCTTGG TGGTCATGGG ACACATATAT GAGCTTTGCA ACACTCACAG CACTCGGTGC     960

ACAATGGTCT TTTCCTCCAG GGCAACGTTC AGTTTCTAGA CGGTCCTTCA ACCACCACAA    1020

GGCGAGAGGA GCCGGGGACC CCAAGGGCCA GAGATGGCAC ACGCTGGTGC CGCTCGGCAC    1080

GGAGACCATC ACCGACAGCT ACATGTCAGC ACCCGCATCA GAGCTGGACA CTAATTTCTT    1140

TACGCTTTAC GTAGCGCAAG GCACAAATAA GTCGCAACAG TACAAGTTCG GCACAGCTAC    1200

ATACGCGCTA AAGGAGCCGG TAATGAAGAG CGATGCATGG GCAGTGGTAC GCGTCCAGTC    1260

GGTCTGGCAG CTGGGTAACA GGCAGAGGCC ATACCCATGG GACGTCAACT GGGCGAACAG    1320

CACCATGTAC TGGGGGACGC AGCCCTGA                                       1348
```

(2) INFORMATION FOR SEQ ID NO: 5:

(i) SEQUENCE CHARACTERISTICS:
        (A) LENGTH: 216 amino acids
        (B) TYPE: amino acid
        (D) TOPOLOGY: unknown (ii) MOLECULE TYPE: protein (iii) HYPOTHETICAL: NO (xi) SEQUENCE DESCRIPTION: SEQ ID NO: 5:

```
Met His Gly Asn Gly Gly Gln Pro Ala Ala Gly Gly Ser Glu Ser Ala
 1               5                  10                  15

Leu Ser Arg Glu Gly Gln Pro Gly Pro Ser Gly Ala Ala Gln Gly Gln
             20                  25                  30

Tyr Ile Ser Asn Glu Arg Ser Pro Arg Arg Tyr Ser Thr Arg Thr Ile
         35                  40                  45

Asn Gly Val Gln Ala Thr Asn Lys Phe Thr Ala Val Gly Asn Pro Ser
 50                  55                  60

Leu Gln Arg Asp Pro Asp Trp Tyr Arg Trp Asn Tyr Asn His Ser Ile
 65                  70                  75                  80

Ala Val Trp Leu Arg Glu Cys Ser Arg Ser His Ala Lys Ile Cys Asn
                 85                  90                  95

Cys Gly Gln Phe Arg Lys His Asn Phe Gln Glu Cys Ala Gly Leu Glu
                100                 105                 110

Asp Arg Ser Thr Gln Ala Ser Leu Glu Glu Ala Ile Leu Arg Pro Leu
            115                 120                 125

Arg Val Gln Gly Lys Arg Ala Lys Arg Lys Leu Asp Tyr His Tyr Ser
130                 135                 140

Gln Pro Thr Pro Asn Arg Lys Lys Ala Tyr Lys Thr Val Arg Trp Gln
145                 150                 155                 160

Asp Glu Leu Ala Asp Arg Glu Ala Asp Phe Thr Pro Ser Glu Glu Asp
                165                 170                 175

Gly Gly Thr Thr Ser Ser Asp Phe Asp Glu Asp Ile Asn Phe Asp Ile
            180                 185                 190

Gly Gly Asp Ser Gly Ile Val Asp Glu Leu Leu Gly Arg Pro Phe Thr
        195                 200                 205

Thr Pro Ala Pro Val Arg Ile Val
    210                 215
```

(2) INFORMATION FOR SEQ ID NO: 6:

(i) SEQUENCE CHARACTERISTICS:
        (A) LENGTH: 651 base pairs
        (B) TYPE: nucleic acid
        (C) STRANDEDNESS: unknown
        (D) TOPOLOGY: unknown (ii) MOLECULE TYPE: DNA (genomic)

(iii) HYPOTHETICAL: NO (xi) SEQUENCE DESCRIPTION: SEQ ID NO: 6:

```
ATGCACGGGA ACGGCGGACA ACCGGCCGCT GGGGGCAGTG AATCGGCGCT TAGCCGAGAG    60

GGGCAACCTG GGCCCAGCGG AGCCGCGCAG GGGCAAGTAA TTTCAAATGA ACGCTCTCCA   120

AGAAGATACT CCACCCGGAC CATCAACGGT GTTCAGGCCA CCAACAAGTT CACGGCCGTT   180

GGAAACCCCT CACTGCAGAG AGATCCGGAT TGGTATCGCT GGAATTACAA TCACTCTATC   240

GCTGTGTGGC TGCCCGAATG CTCGCGCTCC CACGCTAAGA TCTGCAACTG CGGACAATTC   300

AGAAAGCACT GGTTTCAAGA ATGTGCCGGA CTTGAGGACC GATCAACCCA AGCCTCCCTC   360

GAAGAAGCGA TCCTGCGACC CCTCCGAGTA CAGGGTAAGC GAGCTAAAAG AAAGCTTGAT   420

TACCACTACT CCCAGCCGAC CCCGAACCGC AAAAAGGCGT ATAAGACTGT AAGATGGCAA   480
```

```
GACGAGCTCG CAGACCGAGA GGCCGATTTT ACTCCTTCAG AAGAGGACGG TGGCACCACC      540

TCAAGCGACT TCGACGAAGA TATAAATTTC GACATCGGAG GAGACAGCGG TATCGTAGAC      600

GAGCTTTTAG GAAGGCCTTT CACAACCCCC GCCCCGGTAC GTATAGTGTG A              651
```

(2) INFORMATION FOR SEQ ID NO: 7:

(i) SEQUENCE CHARACTERISTICS:
        (A) LENGTH: 121 amino acids
        (B) TYPE: amino acid
        (D) TOPOLOGY: unknown (ii) MOLECULE TYPE: protein (iii) HYPOTHETICAL: NO (xi) SEQUENCE DESCRIPTION: SEQ ID NO: 7:

```
Met Asn Ala Leu Gln Glu Asp Thr Pro Pro Gly Pro Ser Thr Val Phe
  1               5                  10                  15

Arg Pro Pro Thr Ser Ser Arg Pro Leu Glu Thr Pro His Cys Arg Glu
                 20                  25                  30

Ile Arg Ile Gly Ile Ala Gly Ile Thr Ile Thr Leu Ser Leu Cys Gly
                 35                  40                  45

Cys Ala Asn Ala Arg Ala Pro Thr Leu Arg Ser Ala Thr Ala Asp Asn
 50                  55                  60

Ser Glu Ser Thr Gly Phe Lys Asn Val Pro Asp Leu Arg Thr Asp Gln
 65                  70                  75                  80

Pro Lys Pro Pro Ser Lys Lys Arg Ser Cys Asp Pro Ser Glu Tyr Arg
                 85                  90                  95

Val Ser Glu Leu Lys Glu Ser Leu Ile Thr Thr Thr Pro Ser Arg Pro
                100                 105                 110

Arg Thr Ala Lys Arg Arg Ile Arg Leu
                115                 120
```

(2) INFORMATION FOR SEQ ID NO: 8:

(i) SEQUENCE CHARACTERISTICS:
        (A) LENGTH: 366 base pairs
        (B) TYPE: nucleic acid
        (C) STRANDEDNESS: unknown
        (D) TOPOLOGY: unknown (ii) MOLECULE TYPE: DNA (genomic)

(iii) HYPOTHETICAL: NO (xi) SEQUENCE DESCRIPTION: SEQ ID NO: 8:

```
ATGAACGCTC TCCAAGAAGA TACTCCACCC GGACCATCAA CGGTGTTCAG GCCACCAACA       60

AGTTCACGGC CGTTGGAAAC CCCTCACTGC AGAGAGATCC GGATTGGTAT CGCTGGAATT      120

ACAATCACTC TATCGCTGTG TGGCTGCGCG AATGCTCGCG CTCCCACGCT AAGATCTGCA      180

ACTGCGGACA ATTCAGAAAG CACTGGTTTC AAGAATGTGC CGGACTTGAG GACCGATCAA      240

CCCAAGCCTC CCTCGAAGAA GCGATCCTGC GACCCCTCCG AGTACAGGGT AAGCGAGCTA      300

AAAGAAAGCT TGATTACCAC TACTCCCAGC CGACCCCGAA CCGCAAAAAG GCGTATAAGA      360

CTGTAA                                                                 366
```

(2) INFORMATION FOR SEQ ID NO: 9:

(i) SEQUENCE CHARACTERISTICS:
        (A) LENGTH: 12 amino acids (B) TYPE: amino acid
            (D) TOPOLOGY: unknown (ii) MOLECULE TYPE: peptide (iii) HYPOTHETICAL: NO (xi) SEQUENCE DESCRIPTION: SEQ ID NO: 9:

Glu Asp Thr Pro Pro Gly Pro Ser Thr Val Phe Arg
1               5                  10

(2) INFORMATION FOR SEQ ID NO: 10:

(i) SEQUENCE CHARACTERISTICS:
            (A) LENGTH: 12 amino acids
            (B) TYPE: amino acid
            (D) TOPOLOGY: unknown (ii) MOLECULE TYPE: peptide (iii) HYPOTHETICAL: NO (xi) SEQUENCE DESCRIPTION: SEQ ID NO: 10:

Asp Thr Pro Pro Gly Pro Ser Thr Val Phe Arg Pro
1               5                  10

(2) INFORMATION FOR SEQ ID NO: 11:

(i) SEQUENCE CHARACTERISTICS:
            (A) LENGTH: 12 amino acids
            (B) TYPE: amino acid
            (D) TOPOLOGY: unknown (ii) MOLECULE TYPE: peptide (iii) HYPOTHETICAL: NO (xi) SEQUENCE DESCRIPTION: SEQ ID NO: 11:

Thr Pro Pro Gly Pro Ser Thr Val Phe Arg Pro Pro
1               5                  10

(2) INFORMATION FOR SEQ ID NO: 12:

(i) SEQUENCE CHARACTERISTICS:
            (A) LENGTH: 12 amino acids
            (B) TYPE: amino acid
            (D) TOPOLOGY: unknown (ii) MOLECULE TYPE: peptide (iii) HYPOTHETICAL: NO (xi) SEQUENCE DESCRIPTION: SEQ ID NO: 12:

Pro Pro Gly Pro Ser Thr Val Phe Arg Pro Pro Thr
1               5                  10

(2) INFORMATION FOR SEQ ID NO: 13:

(i) SEQUENCE CHARACTERISTICS:
            (A) LENGTH: 12 amino acids
            (B) TYPE: amino acid
            (D) TOPOLOGY: unknown (ii) MOLECULE TYPE: peptide (iii) HYPOTHETICAL: NO (xi) SEQUENCE DESCRIPTION: SEQ ID NO: 13:

Pro Gly Pro Ser Thr Val Phe Arg Pro Pro Thr Ser
1               5                  10

(2) INFORMATION FOR SEQ ID NO: 14:

(i) SEQUENCE CHARACTERISTICS:
        (A) LENGTH: 12 amino acids
        (B) TYPE: amino acid
        (D) TOPOLOGY: unknown (ii) MOLECULE TYPE: peptide (iii) HYPOTHETICAL: NO (xi) SEQUENCE DESCRIPTION: SEQ ID NO: 14:

Gly Pro Ser Thr Val Phe Arg Pro Pro Thr Ser Ser
 1               5                  10

(2) INFORMATION FOR SEQ ID NO: 15:

(i) SEQUENCE CHARACTERISTICS:
        (A) LENGTH: 12 amino acids
        (B) TYPE: amino acid
        (D) TOPOLOGY: unknown (ii) MOLECULE TYPE: peptide (iii) HYPOTHETICAL: NO (xi) SEQUENCE DESCRIPTION: SEQ ID NO: 15:

Pro Ser Thr Val Phe Arg Pro Pro Thr Ser Ser Arg
 1               5                  10

(2) INFORMATION FOR SEQ ID NO: 16:

(i) SEQUENCE CHARACTERISTICS:
        (A) LENGTH: 12 amino acids
        (B) TYPE: amino acid
        (D) TOPOLOGY: unknown (ii) MOLECULE TYPE: peptide (iii) HYPOTHETICAL: NO (xi) SEQUENCE DESCRIPTION: SEQ ID NO: 16:

Gln Glu Cys Ala Gly Leu Glu Asp Arg Ser Thr Gln
 1               5                  10

(2) INFORMATION FOR SEQ ID NO: 17:

(i) SEQUENCE CHARACTERISTICS:
        (A) LENGTH: 12 amino acids
        (B) TYPE: amino acid
        (D) TOPOLOGY: unknown (ii) MOLECULE TYPE: peptide (iii) HYPOTHETICAL: NO (xi) SEQUENCE DESCRIPTION: SEQ ID NO: 17:

Glu Cys Ala Gly Leu Glu Asp Arg Ser Thr Gln Ala
 1               5                  10

(2) INFORMATION FOR SEQ ID NO: 18:

(i) SEQUENCE CHARACTERISTICS:
        (A) LENGTH: 12 amino acids
        (B) TYPE: amino acid
        (D) TOPOLOGY: unknown (ii) MOLECULE TYPE: peptide (iii) HYPOTHETICAL: NO (xi) SEQUENCE DESCRIPTION: SEQ ID NO: 18:

Cys Ala Gly Leu Glu Asp Arg Ser Thr Gln Ala Ser
 1               5                  10

(2) INFORMATION FOR SEQ ID NO: 19:

(i) SEQUENCE CHARACTERISTICS:
        (A) LENGTH: 12 amino acids
        (B) TYPE: amino acid
        (D) TOPOLOGY: unknown (ii) MOLECULE TYPE: peptide (iii) HYPOTHETICAL: NO (xi) SEQUENCE DESCRIPTION: SEQ ID NO: 19:

Ala Gly Leu Glu Asp Arg Ser Thr Gln Ala Ser Leu
 1               5                  10

(2) INFORMATION FOR SEQ ID NO: 20:

(i) SEQUENCE CHARACTERISTICS:
        (A) LENGTH: 12 amino acids
        (B) TYPE: amino acid
        (D) TOPOLOGY: unknown (ii) MOLECULE TYPE: peptide (iii) HYPOTHETICAL: NO (xi) SEQUENCE DESCRIPTION: SEQ ID NO: 20:

Gly Leu Glu Asp Arg Ser Thr Gln Ala Ser Leu Glu
 1               5                  10

(2) INFORMATION FOR SEQ ID NO: 21:

(i) SEQUENCE CHARACTERISTICS:
        (A) LENGTH: 12 amino acids
        (B) TYPE: amino acid
        (D) TOPOLOGY: unknown (ii) MOLECULE TYPE: peptide (iii) HYPOTHETICAL: NO (xi) SEQUENCE DESCRIPTION: SEQ ID NO: 21:

Pro Ser Thr Val Phe Arg Pro Pro Thr Ser Ser Arg
 1               5                  10

(2) INFORMATION FOR SEQ ID NO: 22:

(i) SEQUENCE CHARACTERISTICS:
        (A) LENGTH: 12 amino acids
        (B) TYPE: amino acid
        (D) TOPOLOGY: unknown (ii) MOLECULE TYPE: peptide (iii) HYPOTHETICAL: NO (xi) SEQUENCE DESCRIPTION: SEQ ID NO: 22:

Ser Thr Val Phe Arg Pro Pro Thr Ser Ser Arg Pro
 1               5                  10

(2) INFORMATION FOR SEQ ID NO: 23:

(i) SEQUENCE CHARACTERISTICS:

```
            (A) LENGTH: 12 amino acids
            (B) TYPE: amino acid
            (D) TOPOLOGY: unknown (ii) MOLECULE TYPE: peptide (iii) HYPOTHETICAL: NO (xi) SEQUENCE DESCRIPTION: SEQ ID NO: 23:

Thr Val Phe Arg Pro Pro Thr Ser Ser Arg Pro Leu
 1               5                  10

(2) INFORMATION FOR SEQ ID NO: 24:

(i) SEQUENCE CHARACTERISTICS:
            (A) LENGTH: 12 amino acids
            (B) TYPE: amino acid
            (D) TOPOLOGY: unknown (ii) MOLECULE TYPE: peptide (iii) HYPOTHETICAL: NO (xi) SEQUENCE DESCRIPTION: SEQ ID NO: 24:

Val Phe Arg Pro Pro Thr Ser Ser Arg Pro Leu Glu
 1               5                  10

(2) INFORMATION FOR SEQ ID NO: 25:

(i) SEQUENCE CHARACTERISTICS:
            (A) LENGTH: 12 amino acids
            (B) TYPE: amino acid
            (D) TOPOLOGY: unknown (ii) MOLECULE TYPE: peptide (iii) HYPOTHETICAL: NO (xi) SEQUENCE DESCRIPTION: SEQ ID NO: 25:

Phe Arg Pro Pro Thr Ser Ser Arg Pro Leu Glu Thr
 1               5                  10

(2) INFORMATION FOR SEQ ID NO: 26:

(i) SEQUENCE CHARACTERISTICS:
            (A) LENGTH: 12 amino acids
            (B) TYPE: amino acid
            (D) TOPOLOGY: unknown (ii) MOLECULE TYPE: peptide (iii) HYPOTHETICAL: NO (xi) SEQUENCE DESCRIPTION: SEQ ID NO: 26:

Arg Pro Pro Thr Ser Ser Arg Pro Leu Glu Thr Pro
 1               5                  10

(2) INFORMATION FOR SEQ ID NO: 27:

(i) SEQUENCE CHARACTERISTICS:
            (A) LENGTH: 12 amino acids
            (B) TYPE: amino acid
            (D) TOPOLOGY: unknown (ii) MOLECULE TYPE: peptide (iii) HYPOTHETICAL: NO (xi) SEQUENCE DESCRIPTION: SEQ ID NO: 27:

Pro Pro Thr Ser Ser Arg Pro Leu Glu Thr Pro His
```

(2) INFORMATION FOR SEQ ID NO: 28:

(i) SEQUENCE CHARACTERISTICS:
        (A) LENGTH: 25 base pairs
        (B) TYPE: nucleic acid
        (C) STRANDEDNESS: unknown
        (D) TOPOLOGY: unknown (ii) MOLECULE TYPE: DNA (genomic)

(iii) HYPOTHETICAL: NO (xi) SEQUENCE DESCRIPTION: SEQ ID NO: 28:

AGCTTGATTA CCACTACTCC CTGAG                                            25

(2) INFORMATION FOR SEQ ID NO: 29:

(i) SEQUENCE CHARACTERISTICS:
        (A) LENGTH: 25 base pairs
        (B) TYPE: nucleic acid
        (C) STRANDEDNESS: unknown
        (D) TOPOLOGY: unknown (ii) MOLECULE TYPE: DNA (genomic)

(iii) HYPOTHETICAL: NO (xi) SEQUENCE DESCRIPTION: SEQ ID NO: 29:

TCGACTCAGG GAGTAGTGGT AATCA                                            25

(2) INFORMATION FOR SEQ ID NO:30:

(i) SEQUENCE CHARACTERISTICS:
        (A) LENGTH: 6 amino acids
        (B) TYPE: amino acid
        (C) STRANDEDNESS: Not Relevant
        (D) TOPOLOGY: Not Relevant (ii) MOLECULE TYPE: peptide (iii) HYPOTHETICAL: NO (xi) SEQUENCE DESCRIPTION: SEQ ID NO:30:

Pro Ser Thr Val Phe Arg
1           5

(2) INFORMATION FOR SEQ ID NO:31:

(i) SEQUENCE CHARACTERISTICS:
        (A) LENGTH: 8 amino acids
        (B) TYPE: amino acid
        (C) STRANDEDNESS: Not Relevant
        (D) TOPOLOGY: Not Relevant (ii) MOLECULE TYPE: peptide (iii) HYPOTHETICAL: NO (ix) SEQUENCE DESCRIPTION: SEQ ID NO:31:

Gly Leu Glu Asp Arg Ser Thr Gln
1           5

(2) INFORMATION FOR SEQ ID NO:32:

(i) SEQUENCE CHARACTERISTICS:
        (A) LENGTH: 5 amino acids
        (B) TYPE: amino acid
        (C) STRANDEDNESS: Not Relevant

```
        (D) TOPOLOGY: Not Relevant (ii) MOLECULE TYPE: peptide (iii) HYPOTHETICAL: NO (xi) SEQUENCE DESCRIPTION: SEQ ID NO:32:

Pro Thr Ser Ser Arg
1               5
```